US008858555B2

(12) United States Patent
Crozet et al.

(10) Patent No.: US 8,858,555 B2
(45) Date of Patent: Oct. 14, 2014

(54) DYNAMIC EXTERNAL FIXATOR AND METHODS FOR USE

(75) Inventors: Yves Stephane Crozet, Ramsey, NJ (US); Gurvinderjit Singh Walia, New Delhi (IN); Manoj Kumar Singh, Gurgaon (IN)

(73) Assignee: Stryker Trauma SA (CH)

( * ) Notice: Subject to any disclaimer, the term of this patent is extended or adjusted under 35 U.S.C. 154(b) by 347 days.

(21) Appl. No.: 12/573,310

(22) Filed: Oct. 5, 2009

(65) Prior Publication Data

US 2011/0082458 A1 Apr. 7, 2011

(51) Int. Cl.
A61B 17/62 (2006.01)
A61F 4/00 (2006.01)
A61F 5/04 (2006.01)
A61B 17/64 (2006.01)

(52) U.S. Cl.
CPC ............ *A61B 17/6441* (2013.01); *A61B 17/62* (2013.01)
USPC ........................................................ 606/54

(58) Field of Classification Search
USPC ............. 606/54–59, 96, 104–105; 602/32–40
See application file for complete search history.

(56) References Cited

U.S. PATENT DOCUMENTS

| 6,214 | A | 3/1894 | Yerger |
|---|---|---|---|
| 2,035,952 | A | 3/1936 | Ettinger |
| 2,333,033 | A | 10/1943 | Mraz |
| 2,391,537 | A | 12/1945 | Anderson |
| 2,393,831 | A | 1/1946 | Stader |
| 3,727,610 | A | 4/1973 | Riniker |
| 3,985,127 | A | 10/1976 | Volkov et al. |
| 4,100,919 | A | 7/1978 | Oganesyan et al. |
| 4,185,623 | A | 1/1980 | Volkov et al. |
| 4,338,927 | A | 7/1982 | Volkov et al. |

(Continued)

FOREIGN PATENT DOCUMENTS

| CH | 596826 A5 | 3/1978 |
|---|---|---|
| EP | 611007 A1 | 8/1994 |

(Continued)

OTHER PUBLICATIONS

Biometâ Visionä Footringä System: Surgical Technique, 39 pages, (2008).

(Continued)

*Primary Examiner* — Ellen C Hammond
*Assistant Examiner* — Jacqueline Johanas
(74) *Attorney, Agent, or Firm* — Lerner, David, Littenberg, Krumholz & Mentlik, LLP

(57) ABSTRACT

An external fixation system and method for realigning, compressing or distracting broken bones has a planar ring element with an adjustable device having a body releasably mounted on the ring element. The adjustable device includes a first member for movement in a direction generally perpendicular to the ring element. A second member is pivotally connected to the first member for angular movement with respect to the ring. A third member is mounted on the second member for movement in a direction parallel to the second member and with respect to a circumference of the planar ring element. The method includes inserting k-wires into bone and affixing the k-wires to the ring element and affixing the k-wires to an adjustable device. The pieces of bone are realigned, compressed or distracted by adjusting at least one of a first and second members forming the device.

15 Claims, 22 Drawing Sheets

(56) References Cited

U.S. PATENT DOCUMENTS

| | | | |
|---|---|---|---|
| 4,548,199 A * | 10/1985 | Agee | 606/57 |
| 4,611,586 A * | 9/1986 | Agee et al. | 606/55 |
| 5,067,954 A | 11/1991 | Ilizarov | |
| 5,074,866 A | 12/1991 | Sherman et al. | |
| 5,087,258 A | 2/1992 | Schewior | |
| 5,112,331 A | 5/1992 | Miletich | |
| 5,122,140 A | 6/1992 | Asche et al. | |
| 5,160,335 A | 11/1992 | Wagenknecht | |
| 5,207,676 A | 5/1993 | Canadell et al. | |
| 5,353,504 A | 10/1994 | Pai | |
| 5,358,504 A * | 10/1994 | Paley et al. | 606/56 |
| 5,391,167 A * | 2/1995 | Pong et al. | 606/57 |
| 5,437,666 A * | 8/1995 | Tepic et al. | 606/55 |
| 5,451,225 A | 9/1995 | Ross, Jr. et al. | |
| 5,540,686 A | 7/1996 | Zippel et al. | |
| 5,630,814 A | 5/1997 | Ross, Jr. et al. | |
| 5,658,283 A | 8/1997 | Huebner | |
| 5,662,648 A | 9/1997 | Faccioli et al. | |
| 5,681,309 A | 10/1997 | Ross, Jr. et al. | |
| 5,688,271 A | 11/1997 | Faccioli et al. | |
| 5,702,389 A | 12/1997 | Taylor et al. | |
| 5,713,897 A | 2/1998 | Goble et al. | |
| 5,725,526 A | 3/1998 | Allard et al. | |
| 5,725,527 A | 3/1998 | Biedermann et al. | |
| 5,728,095 A | 3/1998 | Taylor et al. | |
| 5,766,173 A | 6/1998 | Ross, Jr. et al. | |
| 5,776,132 A | 7/1998 | Blyakher | |
| 5,776,173 A | 7/1998 | Madsen, Jr. et al. | |
| 5,788,695 A | 8/1998 | Richardson | |
| 5,797,908 A | 8/1998 | Meyers et al. | |
| 5,843,081 A | 12/1998 | Richardson | |
| 5,846,245 A | 12/1998 | McCarthy et al. | |
| 5,863,292 A * | 1/1999 | Tosic | 606/56 |
| 5,891,143 A | 4/1999 | Taylor et al. | |
| 5,897,555 A | 4/1999 | Clyburn et al. | |
| 5,919,192 A | 7/1999 | Shouts | |
| 5,921,985 A | 7/1999 | Ross, Jr. et al. | |
| 5,928,230 A | 7/1999 | Tosic | |
| 5,931,837 A | 8/1999 | Marsh et al. | |
| 5,971,984 A | 10/1999 | Taylor et al. | |
| 5,976,133 A | 11/1999 | Kraus et al. | |
| 5,997,537 A * | 12/1999 | Walulik | 606/56 |
| 6,007,535 A | 12/1999 | Rayhack et al. | |
| 6,010,501 A | 1/2000 | Raskin et al. | |
| 6,013,081 A * | 1/2000 | Burkinshaw et al. | 606/88 |
| 6,030,386 A | 2/2000 | Taylor et al. | |
| 6,036,691 A | 3/2000 | Richardson | |
| 6,245,071 B1 | 6/2001 | Pierson | |
| 6,328,737 B1 | 12/2001 | Moorcroft et al. | |
| 6,342,052 B1 | 1/2002 | Allende | |
| 6,342,054 B1 | 1/2002 | Mata | |
| 6,423,061 B1 | 7/2002 | Bryant | |
| 6,491,694 B1 * | 12/2002 | Orsak | 606/57 |
| 6,537,275 B2 | 3/2003 | Venturini et al. | |
| 6,610,063 B2 | 8/2003 | Kumar et al. | |
| 6,613,049 B2 | 9/2003 | Winquist et al. | |
| 6,648,891 B2 | 11/2003 | Kim | |
| 6,652,524 B1 | 11/2003 | Weiner | |
| 6,746,448 B2 | 6/2004 | Weiner et al. | |
| 6,784,125 B1 | 8/2004 | Yamakawa et al. | |
| 6,793,655 B2 | 9/2004 | Orsak | |
| 6,860,883 B2 | 3/2005 | Janowski et al. | |
| 6,964,663 B2 | 11/2005 | Grant et al. | |
| 7,048,735 B2 | 5/2006 | Ferrante et al. | |
| 7,147,640 B2 | 12/2006 | Huebner et al. | |
| 7,261,713 B2 | 8/2007 | Langmaid et al. | |
| 7,276,069 B2 | 10/2007 | Biedermann et al. | |
| 7,282,052 B2 * | 10/2007 | Mullaney | 606/59 |
| 7,291,148 B2 | 11/2007 | Agee et al. | |
| 7,311,711 B2 | 12/2007 | Cole | |
| 7,361,176 B2 | 4/2008 | Cooper et al. | |
| 7,422,593 B2 | 9/2008 | Cresina et al. | |
| 7,449,023 B2 | 11/2008 | Walulik et al. | |
| 7,468,063 B2 | 12/2008 | Walulik et al. | |
| 7,479,142 B2 | 1/2009 | Weiner et al. | |
| 7,491,008 B2 | 2/2009 | Thomke et al. | |
| 7,507,240 B2 | 3/2009 | Olsen | |
| 7,527,626 B2 | 5/2009 | Lutz et al. | |
| 7,575,575 B2 | 8/2009 | Olsen et al. | |
| 7,578,822 B2 | 8/2009 | Rezach et al. | |
| RE40,914 E | 9/2009 | Taylor et al. | |
| 7,608,074 B2 | 10/2009 | Austin et al. | |
| 7,632,271 B2 | 12/2009 | Baumgartner et al. | |
| 7,699,848 B2 | 4/2010 | Hoffman et al. | |
| 7,708,736 B2 | 5/2010 | Mullaney | |
| 7,749,224 B2 | 7/2010 | Cresina et al. | |
| 7,763,020 B2 | 7/2010 | Draper | |
| 7,803,158 B2 * | 9/2010 | Hayden | 606/80 |
| 7,806,843 B2 | 10/2010 | Marin | |
| 7,815,586 B2 | 10/2010 | Grant et al. | |
| 7,875,030 B2 | 1/2011 | Hoffmann-Clair et al. | |
| 7,881,771 B2 | 2/2011 | Koo et al. | |
| 7,887,498 B2 | 2/2011 | Marin | |
| 7,887,537 B2 | 2/2011 | Ferrante et al. | |
| 7,931,650 B2 | 4/2011 | Winquist et al. | |
| 7,938,829 B2 | 5/2011 | Mullaney | |
| 7,955,333 B2 | 6/2011 | Yeager | |
| 7,955,334 B2 | 6/2011 | Steiner et al. | |
| 7,985,221 B2 | 7/2011 | Coull et al. | |
| 8,029,505 B2 | 10/2011 | Hearn et al. | |
| 8,057,474 B2 | 11/2011 | Knuchel et al. | |
| 8,114,077 B2 | 2/2012 | Steiner et al. | |
| 8,137,347 B2 | 3/2012 | Weiner et al. | |
| 8,142,432 B2 | 3/2012 | Matityahu | |
| 8,147,490 B2 | 4/2012 | Bauer | |
| 8,147,491 B2 | 4/2012 | Lavi | |
| 8,157,800 B2 | 4/2012 | Vvedensky et al. | |
| 8,172,849 B2 | 5/2012 | Noon et al. | |
| 8,182,483 B2 | 5/2012 | Bagnasco et al. | |
| 8,187,274 B2 | 5/2012 | Schulze | |
| 8,192,434 B2 | 6/2012 | Huebner et al. | |
| 8,202,273 B2 | 6/2012 | Karidis | |
| 8,241,285 B2 | 8/2012 | Mullaney | |
| 8,251,937 B2 | 8/2012 | Marin | |
| 8,282,652 B2 | 10/2012 | Mackenzi et al. | |
| 2001/0049526 A1 | 12/2001 | Venturini et al. | |
| 2002/0013584 A1 | 1/2002 | Termaten | |
| 2002/0042613 A1 | 4/2002 | Mata | |
| 2002/0165543 A1 | 11/2002 | Winquist et al. | |
| 2003/0069580 A1 | 4/2003 | Langmaid et al. | |
| 2003/0106230 A1 | 6/2003 | Hennessey | |
| 2003/0109879 A1 | 6/2003 | Orsak | |
| 2003/0181911 A1 | 9/2003 | Venturini | |
| 2003/0191466 A1 | 10/2003 | Austin et al. | |
| 2003/0216734 A1 | 11/2003 | Mingozzi et al. | |
| 2003/0225406 A1 | 12/2003 | Weiner et al. | |
| 2004/0073211 A1 | 4/2004 | Austin et al. | |
| 2004/0097944 A1 | 5/2004 | Koman et al. | |
| 2004/0116926 A1 | 6/2004 | Venturini et al. | |
| 2004/0133199 A1 | 7/2004 | Coati et al. | |
| 2004/0133200 A1 | 7/2004 | Ruch et al. | |
| 2005/0043730 A1 | 2/2005 | Janowski et al. | |
| 2005/0059968 A1 | 3/2005 | Grant et al. | |
| 2005/0113829 A1 | 5/2005 | Walulik et al. | |
| 2005/0119656 A1 | 6/2005 | Ferrante et al. | |
| 2005/0149018 A1 | 7/2005 | Cooper et al. | |
| 2005/0234448 A1 | 10/2005 | McCarthy | |
| 2006/0155276 A1 | 7/2006 | Walulik et al. | |
| 2006/0229605 A1 | 10/2006 | Olsen | |
| 2006/0235383 A1 | 10/2006 | Hollawell | |
| 2006/0276786 A1 | 12/2006 | Brinker | |
| 2006/0287652 A1 | 12/2006 | Lessig et al. | |
| 2007/0038217 A1 | 2/2007 | Brown et al. | |
| 2007/0043354 A1 | 2/2007 | Koo et al. | |
| 2007/0049930 A1 | 3/2007 | Hearn et al. | |
| 2007/0055233 A1 * | 3/2007 | Brinker | 606/54 |
| 2007/0123857 A1 | 5/2007 | Deffenbaugh et al. | |
| 2007/0161983 A1 | 7/2007 | Cresina et al. | |
| 2007/0161984 A1 | 7/2007 | Cresina et al. | |
| 2007/0225704 A1 | 9/2007 | Ziran et al. | |
| 2007/0233061 A1 | 10/2007 | Lehmann et al. | |
| 2007/0255280 A1 | 11/2007 | Austin et al. | |
| 2007/0282338 A1 | 12/2007 | Mullaney | |
| 2008/0228185 A1 | 9/2008 | Vasta et al. | |

(56) References Cited

U.S. PATENT DOCUMENTS

| | | |
|---|---|---|
| 2008/0269741 A1 | 10/2008 | Karidis |
| 2009/0018541 A1 | 1/2009 | Lavi |
| 2009/0036890 A1 | 2/2009 | Karidis |
| 2009/0036891 A1 | 2/2009 | Brown et al. |
| 2009/0105621 A1 | 4/2009 | Boyd et al. |
| 2009/0131935 A1 | 5/2009 | Yeager |
| 2009/0177198 A1 | 7/2009 | Theodoros et al. |
| 2009/0198234 A1 | 8/2009 | Knuchel et al. |
| 2009/0264883 A1 | 10/2009 | Steiner et al. |
| 2009/0287212 A1 | 11/2009 | Hirata et al. |
| 2009/0312757 A1 | 12/2009 | Kehres et al. |
| 2010/0145336 A1 | 6/2010 | Draper |
| 2010/0179548 A1 | 7/2010 | Marin |
| 2010/0191239 A1 | 7/2010 | Sakkers et al. |
| 2010/0234844 A1 | 9/2010 | Edelhauser et al. |
| 2010/0249779 A1 | 9/2010 | Hotchkiss et al. |
| 2010/0280516 A1 | 11/2010 | Taylor |
| 2010/0298827 A1 | 11/2010 | Cremer et al. |
| 2010/0305568 A1 | 12/2010 | Ross et al. |
| 2010/0312243 A1 | 12/2010 | Ross et al. |
| 2010/0331840 A1 | 12/2010 | Ross et al. |
| 2011/0060336 A1 | 3/2011 | Pool et al. |
| 2011/0066151 A1 | 3/2011 | Murner et al. |
| 2011/0082458 A1 | 4/2011 | Crozet et al. |
| 2011/0098707 A1 | 4/2011 | Mullaney |
| 2011/0112533 A1 | 5/2011 | Venturini et al. |
| 2011/0118737 A1 | 5/2011 | Vasta et al. |
| 2011/0118738 A1 | 5/2011 | Vasta et al. |
| 2011/0172663 A1 | 7/2011 | Mullaney |
| 2011/0172664 A1 | 7/2011 | Bagnasco et al. |
| 2011/0245830 A1 | 10/2011 | Zgonis et al. |
| 2011/0313418 A1 | 12/2011 | Nikonovas |
| 2011/0313419 A1 | 12/2011 | Mullaney |
| 2012/0004659 A1 | 1/2012 | Miller et al. |
| 2012/0041439 A1 | 2/2012 | Singh et al. |
| 2012/0078251 A1 | 3/2012 | Benenati et al. |
| 2012/0089142 A1 | 4/2012 | Mullaney et al. |
| 2012/0095462 A1 | 4/2012 | Miller |
| 2012/0136355 A1 | 5/2012 | Wolfson |
| 2012/0143190 A1 | 6/2012 | Wolfson |

FOREIGN PATENT DOCUMENTS

| | | |
|---|---|---|
| EP | 2417923 A1 | 2/2012 |
| EP | 2417924 A1 | 2/2012 |
| FR | 2576774 A1 | 8/1986 |
| WO | 2007/111576 A2 | 10/2007 |
| WO | 2010104567 A1 | 9/2010 |
| WO | 2012102685 A1 | 8/2012 |

OTHER PUBLICATIONS

Nanua et al., IEEE Transactions on Robotics and Automation, vol. 6, No. 4, pp. 438-444, Aug. 1990.
European Search Report, EP 10 172 523 dated Mar. 25, 2011.
European Search Report, EP 11176512, dated Sep. 19, 2011.
European Search Report, EP 11176566, dated Sep. 20, 2011.
Partial European Search Report for Application No. EP13180720 dated Dec. 3, 2013.

\* cited by examiner

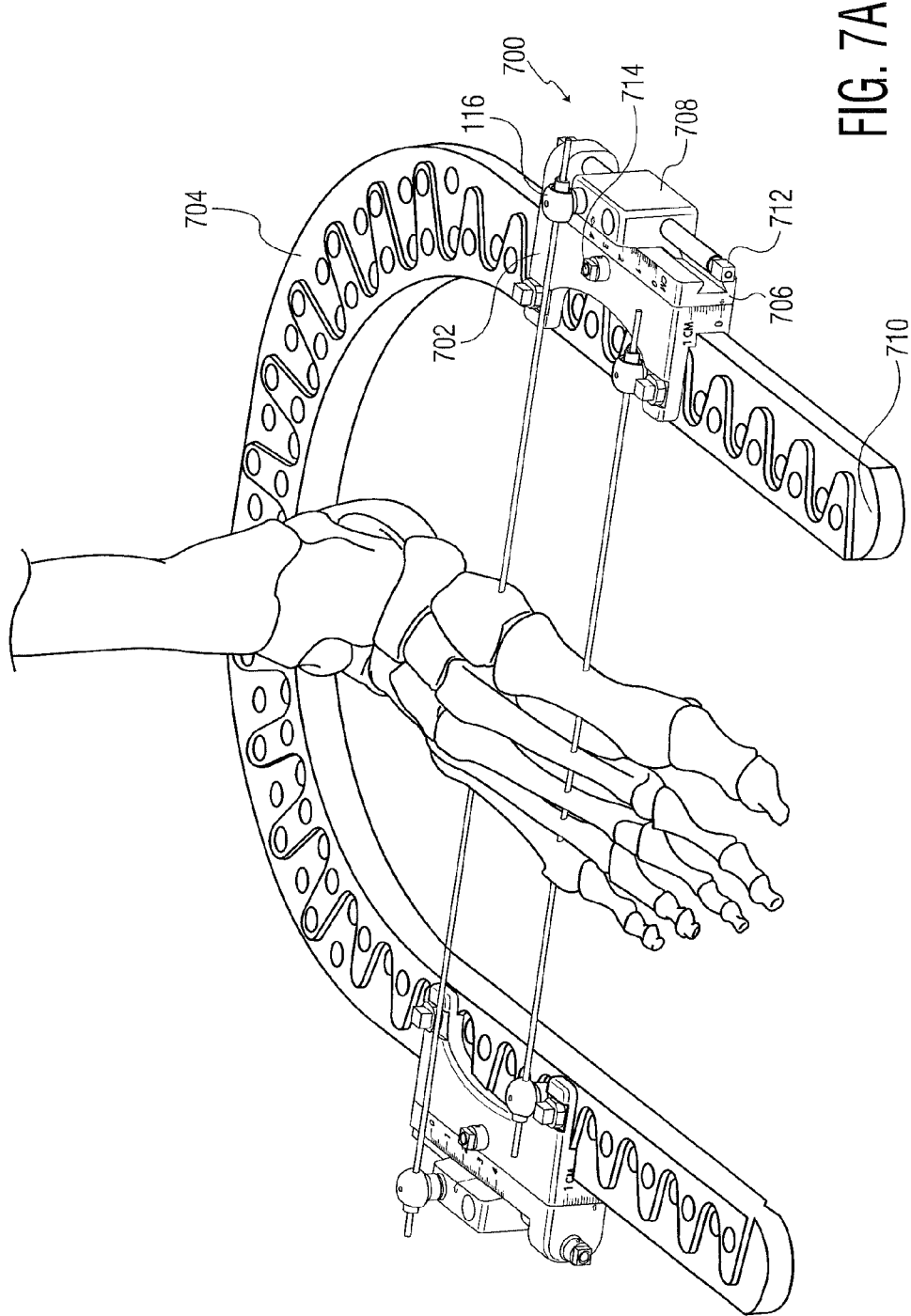

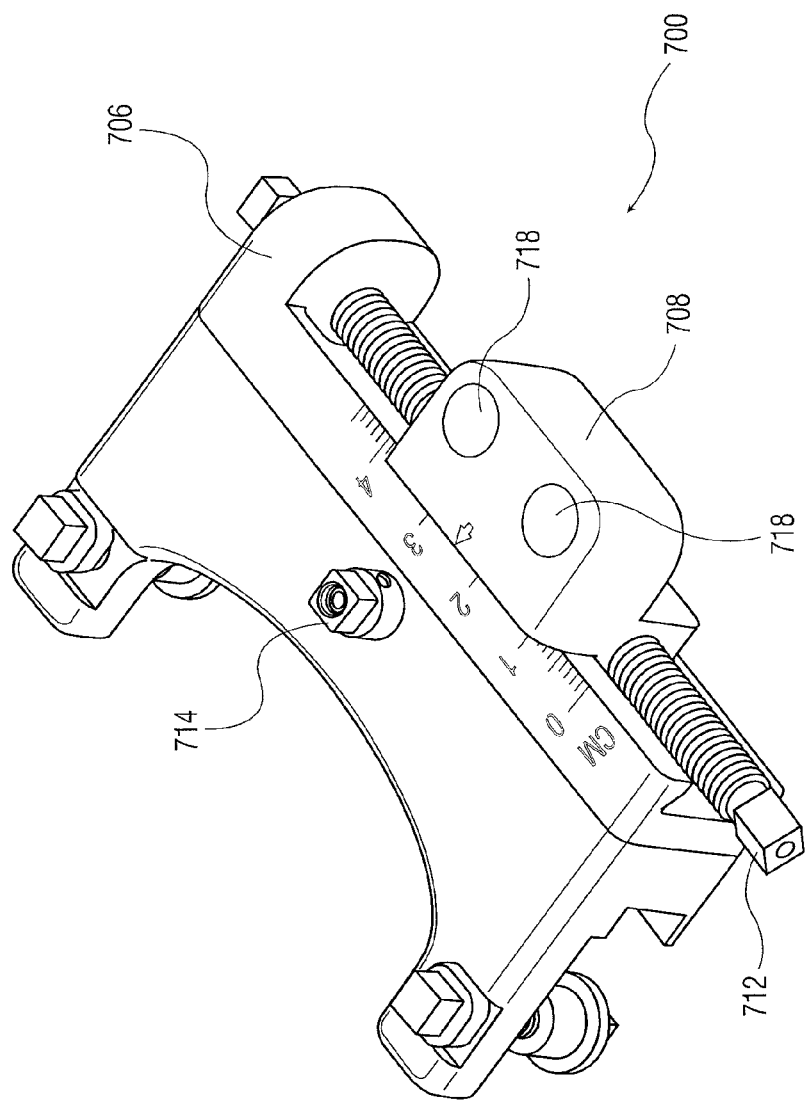

DYNAMIC EXTERNAL FIXATOR AND METHODS FOR USE

BACKGROUND OF THE INVENTION

During reconstruction of a fractured or broken bone it is necessary to keep the repaired bone in an immobilized and stable state during the healing process. Further, the pieces of broken bones need to be encouraged to grow together. That is, the bone may be broken into multiple pieces and those pieces need to be moved together to promote proper healing. Presently, this is accomplished using a rigid body such as an external fixation ring or frame and various fixation components (e.g., wires, pins, etc.). These fixation components extend from the ring and immobilize the bone and move the bone into proper realignment.

More specifically, the rigid body used in foot and/or ankle reconstruction is a foot frame. Typically, foot frames have an open ring member. This open ring member typically is a single U-shaped frame designed to connect with half pins or wires (e.g., Kirschner or k-wires) passed through the broken or fractured bones. To encourage the bones together, these wires are implanted through particular pieces of the bone (e.g., the foot and/or ankle) and are attached at their ends to the open ring member. These wires are, typically, attached to the open ring member by wire/rod nuts. Further, these wires immobilize and/or apply force to the particular bones in order to move the bones together into proper alignment.

Presently, in order to provide a force to move the bones these wires are bent prior to being attached to the open ring member. Thus, by applying tension to the wire, the wire straightens creating a force on the bone and encouraging the bones together. However, this technique provides little control over the movement of the wire and amount of force on the bone.

Accordingly, a need exists to develop a device and method for accurately moving the wires so as to move the bones together in a controlled manner.

BRIEF SUMMARY OF THE INVENTION

Disclosed herein is an external fixation system. The external fixation system includes a ring element having a planar portion and an adjustable device having a body releasably mounted on the planar portion of the ring element. The adjustable device further includes a first member mounted on the body for movement in a direction generally perpendicular to the planar ring portion; a second member pivotally mounts on the first member for angular movement with respect to the body; a third member mounts on the second member for movement with respect to a circumference of the ring element; and a bone engaging element mounts on the third member.

Further, disclosed herein is an external fixation system including a ring element having a planar portion; and an adjustable device including a body, a first member and a second member. The body being releasably mounted on the ring element. Further, the first member is capable of moving in a direction perpendicular to a planar surface on the ring element and the second member is capable of linear motion about the circumference of the ring element. The body, first member, and second member each include a planar surface; and the planar surface of the body contacts a first planar surface of the first member and second planar surface on the first member is in contact with a first planar surface of the second member.

Also disclosed herein is a method for realigning a broken bone. The method includes providing an external fixation device having a ring member, a first adjustable device, and a second adjustable device. The first adjustable device having a body attached to the ring member, a first member mounted on the body, a second member mounted on the first member, and a third member mounted on the second member. The second adjustable device having a body attached to the ring member, a first member mounted on the body, a second member mounted on the first member, and a third member attached to the second member. Further, a first k-wire or half pin is inserted through a first piece of a broken bone and the first k-wire or half pin is affixed to the ring member. A second k-wire or half pin is inserting through a second piece of (broken) bone and the second k-wire is affixed to the first and second adjustable devices. Adjusting at least one of the first and second adjustable devices realigns the broken bone.

The dynamic fixator described herein can be used to gradually correct a traumatized bone (i.e., a bone that is broken or fractured). The fixator provides accurate multi axis movement (i.e., movement in two to three different axes-linear, vertical, and angular). This multi axis movement is used in repairing traumatized bone by, for example, realigning two pieces of a traumatized bone. Note: sometimes the wires are not in the broken bones. They may be in healthy bones on either sides of the fractured bones For example, two pieces of a (traumatized) bone can be realigned by bringing the pieces of bone together. The bones are brought together by having a first and second k-wire pass through a first and second piece of the (traumatized) bone and having the first and second k-wires attached to one of a rigid body (e.g., ring element) or an adjustable device wherein the traumatized bone is realigned by moving the adjustable device in at least one axis. More specifically, after passing the first k-wire through the traumatized bone, both the first and second ends of the first k-wire are attached to a ring element. With the first piece of traumatized bone secured, a second k-wire is passed through a second piece of traumatized bone. After passing the second k-wire through the second piece of traumatized bone, the first end of the second k-wire is attached to a first adjustable device and the second end of the second k-wire is attached to a second adjustable device. Keeping the first k-wire attached to the rigid body the second k-wire can be moved in accurate multi axis movement by adjusting the first and second adjustable devices. Moving at least one of the first and second adjustable devices causes the second k-wire to move thereby moving the traumatized bone into a desired position (e.g., proper alignment).

In some embodiments, the adjustable device is capable of motion in three different directions. For example, the adjustable device is capable of linear, vertical, and angular motion. In other embodiments, the adjustable device is capable of motion in two different directions. For example, the adjustable device is capable of linear and vertical motion, however, it can not move angularly. It will be apparent that the adjustable device can produce any combination of linear, vertical, and angular motion. Further, although described as having the second k-wire attached to a first and second adjustable device the first end or second end of the second k-wire can be attached to the rigid body. Further still, as an alternative, both the first and the second k-wires can be attached to adjustable devices, the rigid body, or a combination of an adjustable device and the rigid body. Lastly, although depicted as only one or two adjustable devices, any number of adjustable devices can be attached to the rigid body.

As used herein when referring to bones or other parts of the body, the term "proximal" means close to the heart and the term "distal" means more distant from the heart. The term "inferior" means toward the feet and the term "superior" means toward the head. The term "anterior" means toward the front part or the face and the term "posterior" means toward the back of the body. The term "medial" means toward the midline of the body and the term "lateral" means away from the midline of the body.

BRIEF DESCRIPTION OF THE DRAWINGS

These and other aspects of this invention are explained and elaborated through reference to the embodiments described as examples below. Examples of embodiments are described in the following with reference to the following drawings.

FIGS. 7A-7B are isometric views similar to FIGS. 1A *and* 1B showing the adjustable device from two different positions;

FIG. 8A is an isometric view of an alternate adjustable device allowing two degrees of movement;

DETAILED DESCRIPTION

Figure 1A:
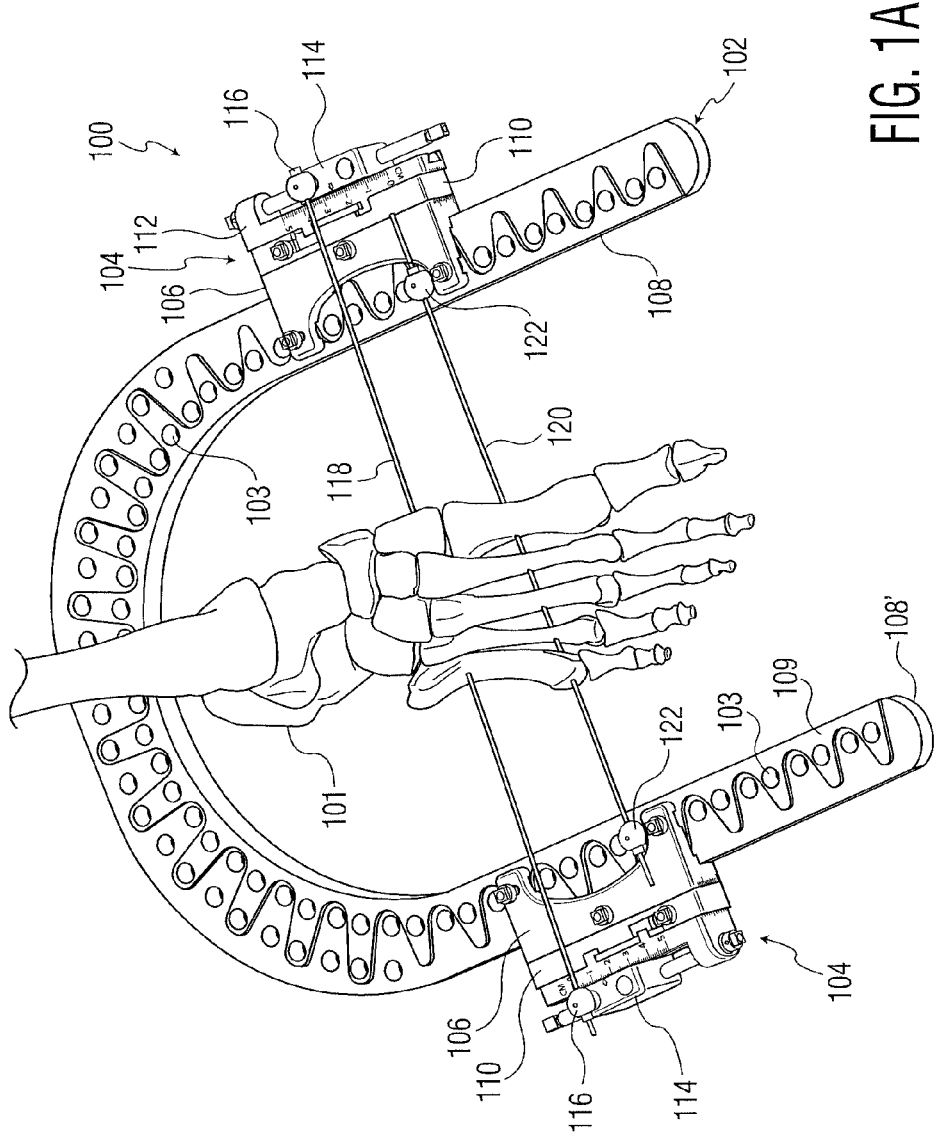
FIGS. 1A-1B show an isometric view of an external fixation device having a ring element and two adjustable devices having k-wires mounted thereon attached to the parts according to the present invention.
Figure 1B:
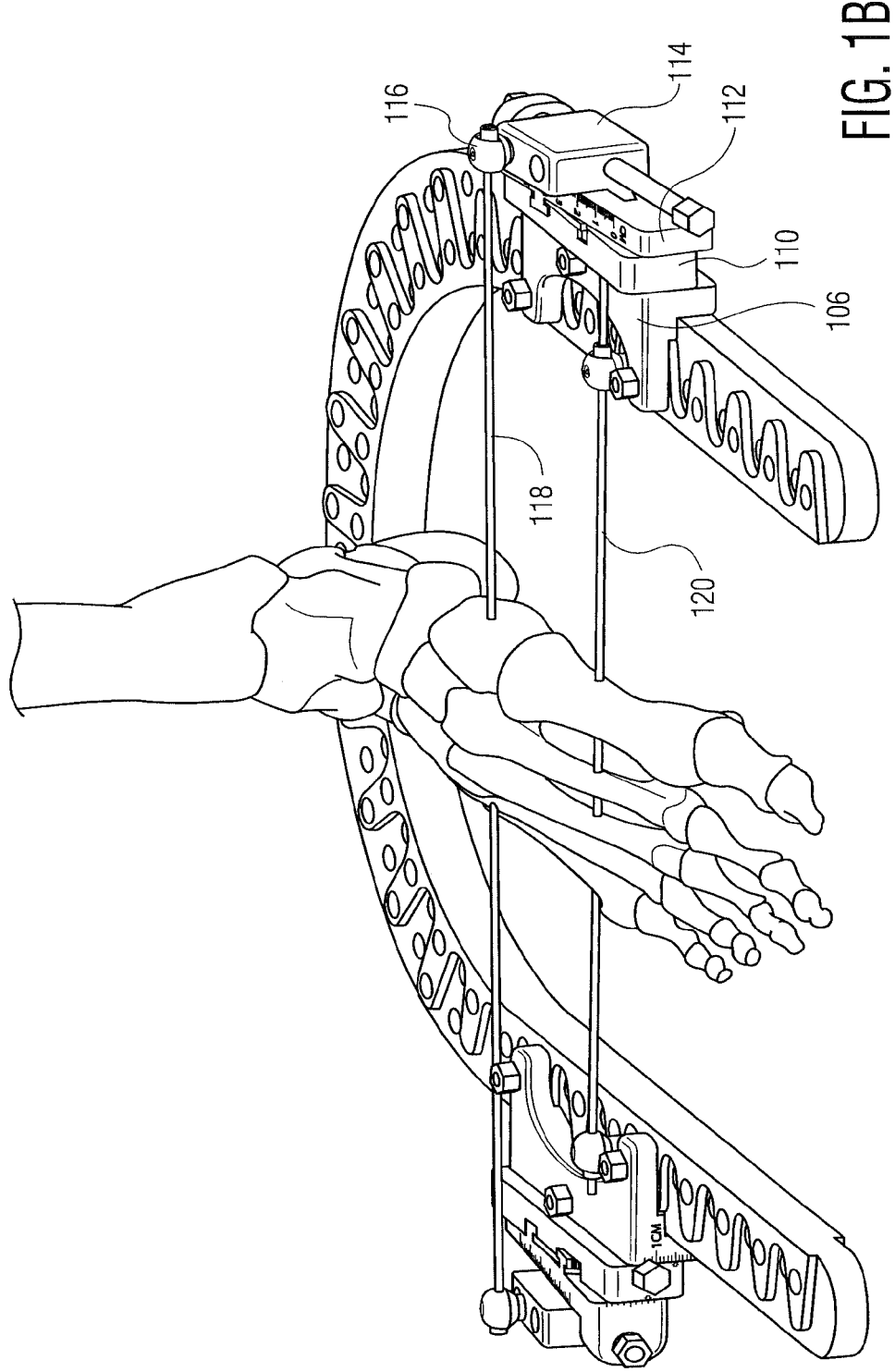

Referring to FIGS. 1A-1B, in accordance with a preferred embodiment of the present invention, an isometric view of a dynamic external fixator generally denoted as 100 is shown mounted on a foot 101 by pins. Dynamic external fixator 100 includes a U-shaped ring element 102 having a plurality of mounting holes 103 with at least one adjustable device 104, and preferably two, releasably attached to a pair of mounting holes 103. Adjustable device 104 includes a body 106 releasably attached to arms 108, 108' of ring element 102. The adjustable device further includes a first member 110 slidably mounted on body 106 capable of providing movement in a direction perpendicular to a proximal surface 109 of arm 108, 108' of ring element 102. Further, a second member 112 pivotally mounts on first member 110 for providing angular movement (i.e., rotation) with respect to first member 110. Further still, a third member 114 mounts on second member 112 providing linear movement along arms 108, 108'. Preferably one or more wire engagement elements 116 attach first or second k-wires 118 that pass through a fractured bone respectively. The wire engagement elements are mounted to third member 114 and/or to ring 102 directly. For example, as shown, first k-wire 118 attaches to a standard bone engagement element 116. Further, a second k-wire 120 can attach directly to ring element 102. For example, as shown, second k-wire 120 attaches to ring element 102 by being clamped in a standard ring engagement element 122 mounted in a hole 103.

Preferably first and second k-wires 118,120 are substantially smooth pins with a drill tip. In some instances, however, first and second k-wires 118,120 may not include a drill tip. Further, first and second k-wires 118,120 can be made of any suitable material, such as, but not limited to, stainless steel, titanium, and titanium alloy. Further, first and second k-wires 118, 120 can connect to bone engagement element 116 and ring engagement element 122 by being inserted through a hole (not shown) in bone engagement element 116 or ring engagement element 122 and applying a force on first or second k-wires 118, 120 by, for example, a set screw (not shown). Alternatively, bone engagement element 116 or ring engagement element 122 can be a wire/rod nut. Any reasonable method for attaching first and second k-wires 118, 120 to bone engagement element 116 or ring engagement element 122 can be used.

Ring element 102 can be a substantially monolithic material designed to releasably attach to at least one adjustable device 104. Ring element 102 can be made of metal (e.g., stainless steel, titanium, etc.), composites (e.g., Carbon PEEK, etc.), or any other material deemed suitable. Further, although described as a u-shaped ring, ring element 102 can include any shape that allows at least one adjustable device to be releasably connected to it. For example, ring element 102 can be a circle shape, horseshoe shape, square shape, rectangle shape, or any other shape deemed suitable. Ring element 102 preferably is planer creating a relatively flat surface on ring element 102. This flat surface is used to provide a flat surface to releasably attach ring element 102 with adjustable device 104. Such a ring can have four levels as shown in U.S. patent application Ser. No. 12/157,612 filed Jun. 11, 2008, the disclosure of which is incorporated herein by reference.

Figure 2A:
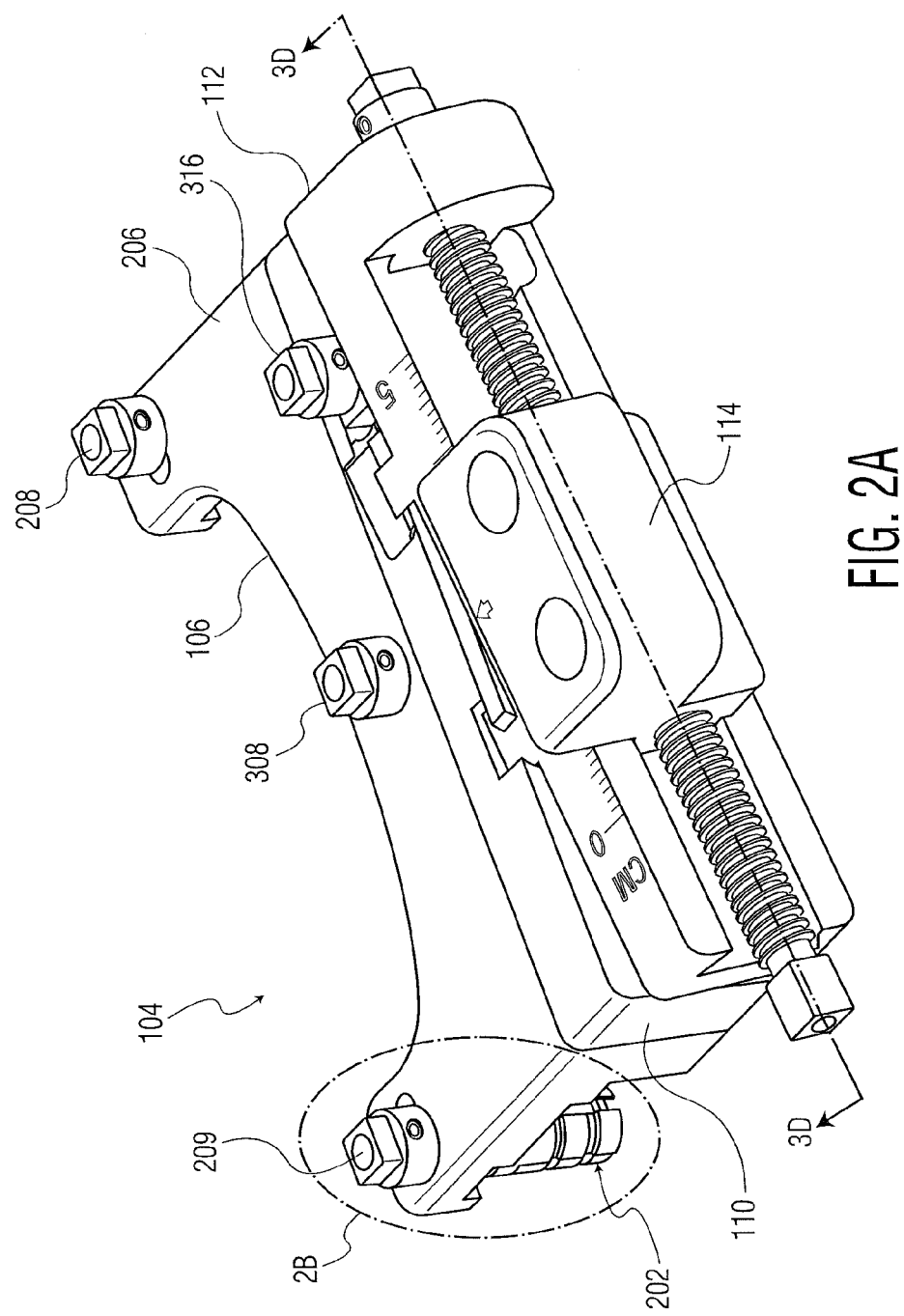
FIG. 2A shows an enlarged isometric view of the adjustable device shown in FIG. 1.

Referring to FIG. 2A, adjustable device 104 is shown in greater detail. Adjustable device 104 has a body 106 with a pair of expandable connectors 202 having drive heads 208, 209, that releasably connect adjustable device 104 to holes 103 of ring element 102. Attached to body 106 is first member 110 which slidably mounts on body 106. While mounted on body 106, when fixed on ring 102, first member 110 can move up and down with respect to top planar surface 206 of body 106. That is, first member 110 can move in a direction perpendicular to upper surface 206 of body 106 and the plane of the ring 102. This is accomplished by the rotating threaded screw shaft 302 as will be described below. Further, because, in the preferred embodiment, surface 206 of body 106 is parallel to the plane of ring element 102 (see, FIGS. 1A-1B) first member 110 moves in a direction perpendicular to the plane of ring element 102.

Figure 2B:
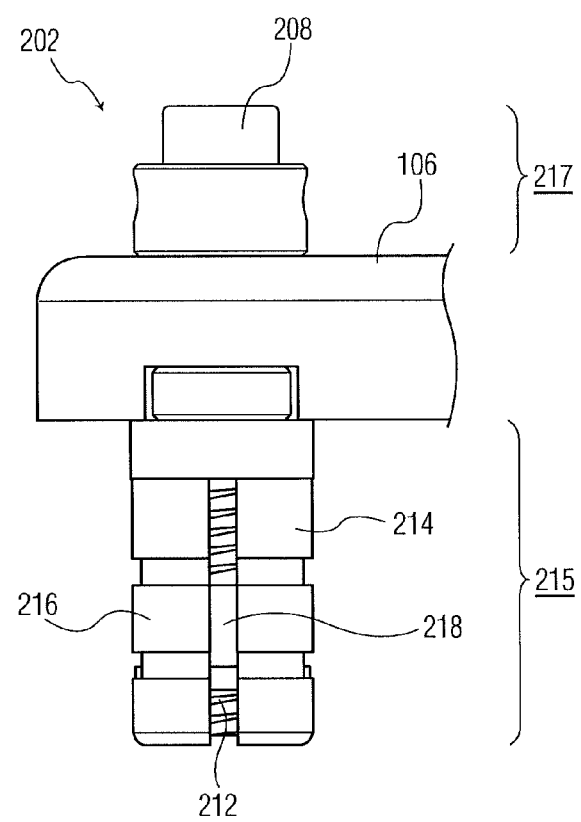
FIG. 2B shows an enlarged view of area A of FIG. 2A showing a ring coupling element.

Referring to FIG. 2B an exemplary ring element connector is displayed. As shown, preferred connector 202 includes a lower outer portion 215 located under body 106 split into two sections 214, 216 and an inner portion 217 with a drive head 208 located above body 106 for engaging a drive tool. Further, inner portion 217 has a threaded shaft 212 coupled to drive head 208 and extends between the two halves 214, 216. Threaded shaft 212 includes tapered nut 218 which when moved toward body 106 caused sections 214 and 216 to expand. After connector 202A is placed through body 106 and into hole 103 in the ring element 102, nut 218 is threaded on the bottom of threaded shaft 212. As drives 208, 209 are rotated nut 218 causes the two halves 214,216 to expand thereby securing the adjustable device to the ring element. Although described as two halves the split portion can include any number of sections (e.g., three or four sections).

Figure 2C:
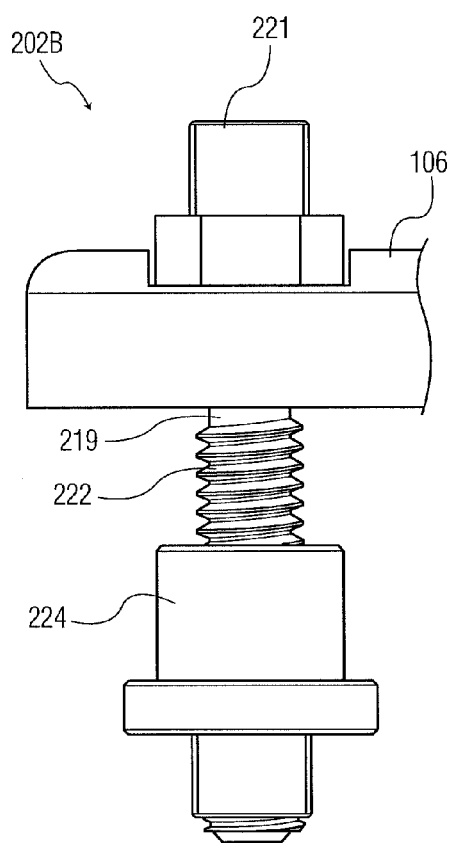
FIG. 2C is an enlarged view of an alternate ring coupling element of the present invention used in FIG. 3A.

Referring to FIG. 2C there is shown an alternative ring element connector 202B. As shown, ring connector 202B can include a shaft 219 with a screw thread portion 222 and a drive head 221. The threaded shaft portion 222 is inserted through the bore in body 106 until drive head 221 comes into contact with upper surface body 106. Threaded shaft portion 222 is further inserted through an opening 103 in ring element 102 and threaded into a nut 224. As threaded shaft portion 222 is threaded into nut 224 adjustable device 104 is secured onto ring element 102. Further, any method of releasably securing adjustable device 104 to the ring element can be used. For example, the adjustable device can be releasably attached to the ring element by a screw and nut, a bolt assembly, or any other securing method deemed suitable.

Figure 3A:
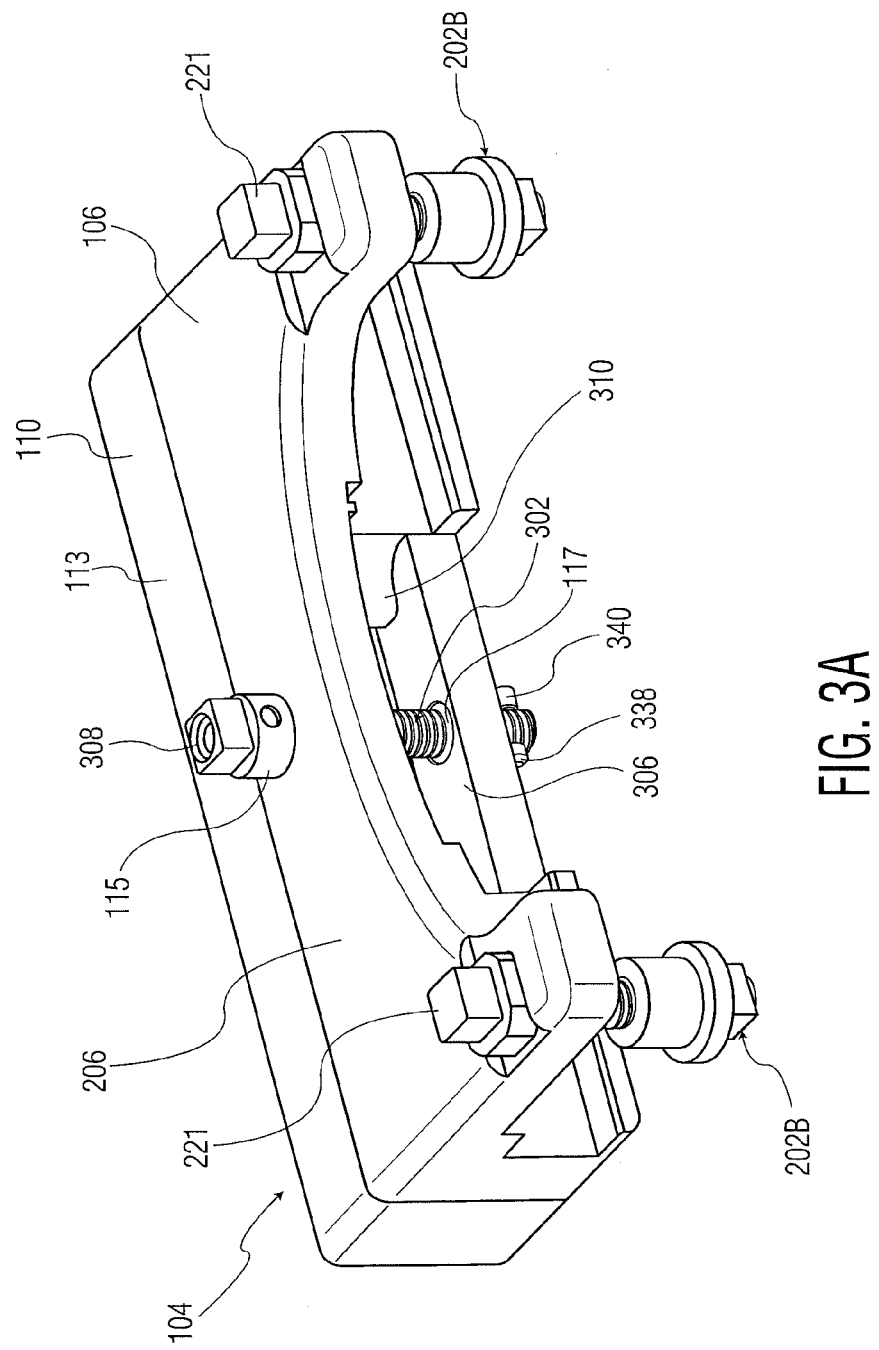
FIG. 3A is an isometric view of an adjustable device showing the interaction between a first member and a body that enables the first member to move up and down (i.e., perpendicular to a planar surface on the ring element)

Referring to FIG. 3A, a rear view of two parts of the preferred adjusting device 104 is shown. The two parts are members 110 and 106. First member 110 has a first portion 113 and a central portion 306 which can move in a direction perpendicular to the plane of ring element 102 by rotating a screw shaft 302 via drive head 308. Screw shaft 302 is placed through a hole 115 in body 106 and is threaded into a second threaded hole 117 located in central flange 306 extending rearwardly from first portion 113 of first member 110. Shaft 302 has an end 338 with a pin 340 to ensure the assembly does not come apart during use. In use, a user rotates a drive head 308 causing screw 302 to thread into the second hole thereby moving first member 110 up and down with respect to body 106 (i.e., perpendicular to planar surface 206 of body 106 and perpendicular to the plane of ring element 102). Alternatively, although screw shaft 302 is described as threaded into a second hole in member 110, screw 302 may thread into a threaded hole in body 106 and fixed in part 306. It will be understood that any method of making first member 110 move up and down with respect to body 106 can be used. Further, increasing the number of threads on screw shaft 302 increases the number of rotations needed to move first member 110 up and down. Thus, increasing the number of threads increases the precision of up and down movement.

In some embodiments, flange 306 extending from first member 110 is designed to ride along a protruding track 310 extending from body 106. Riding on track 310 reduces the amount of movement in an undesired direction. Further, any method of mating first member 110 with body 106 designed to decrease movement in an undesired direction can be used. For example, first member 110 and body 106 can include any male-female mating features (e.g., tongue and groove or dovetail) for providing guided movement up and down.

Figure 4:
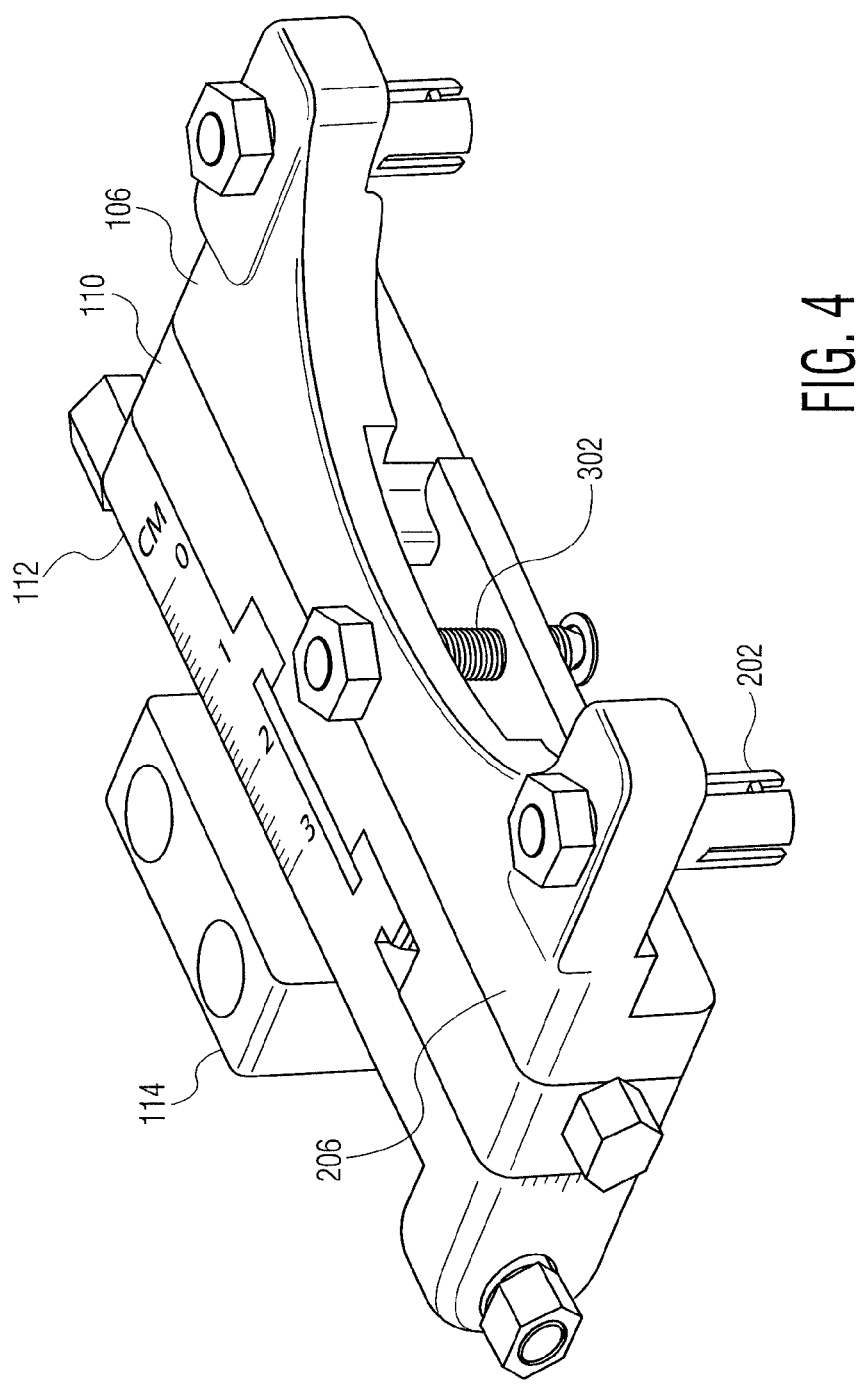
FIG. 4 is a rear view of the adjustable device of FIG. 4 in a first position.
Figure 6A:
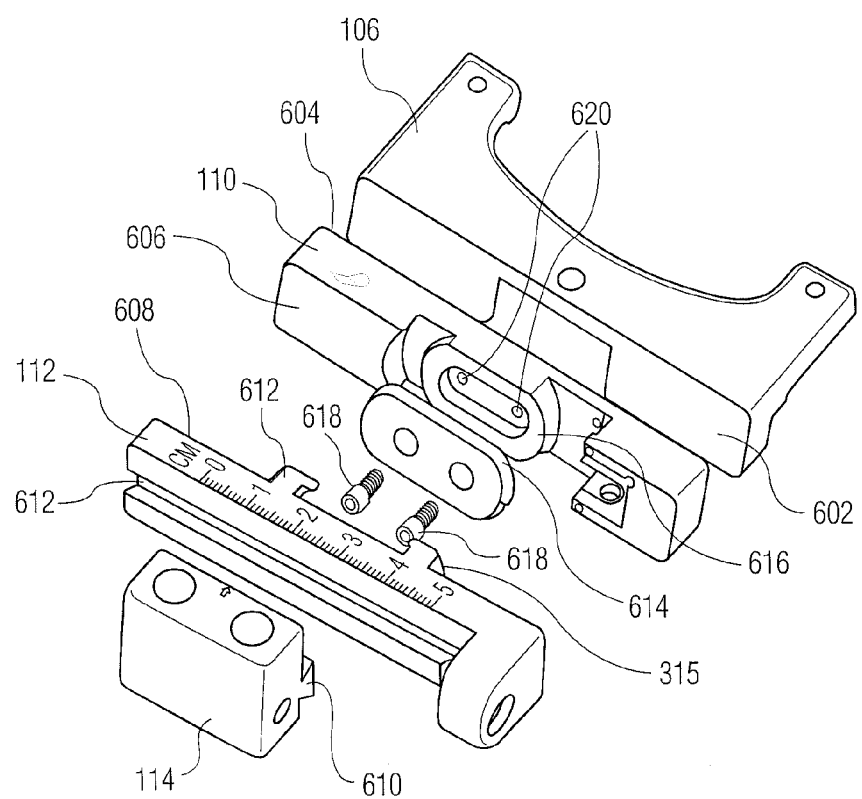
FIGS. 6A and 6B are exploded views of an adjustable device of FIG. 2A showing the body, the first member, the second member, and the third member.

Referring to FIGS. 2A, 4 and 6A, second member 112 is rotatably mounted on first member 110. While mounted on first member 110, second member 112 can rotate through a range of angles with respect to first member 110. That is, second member 112 is pivotally mounted by guide tracks 612 on first member 110 and can rotate with respect to first member 110. For example, in the preferred embodiment, second member 112 can pivot up to 120 degrees around its center on guide 614 mounted on first member 110 as shown in FIG. 6A. That is, second member 112 can, for example, rotate 60 degrees from parallel in an upward direction and 60 degrees in a downward direction with respect to surface 306.

Figure 3B:
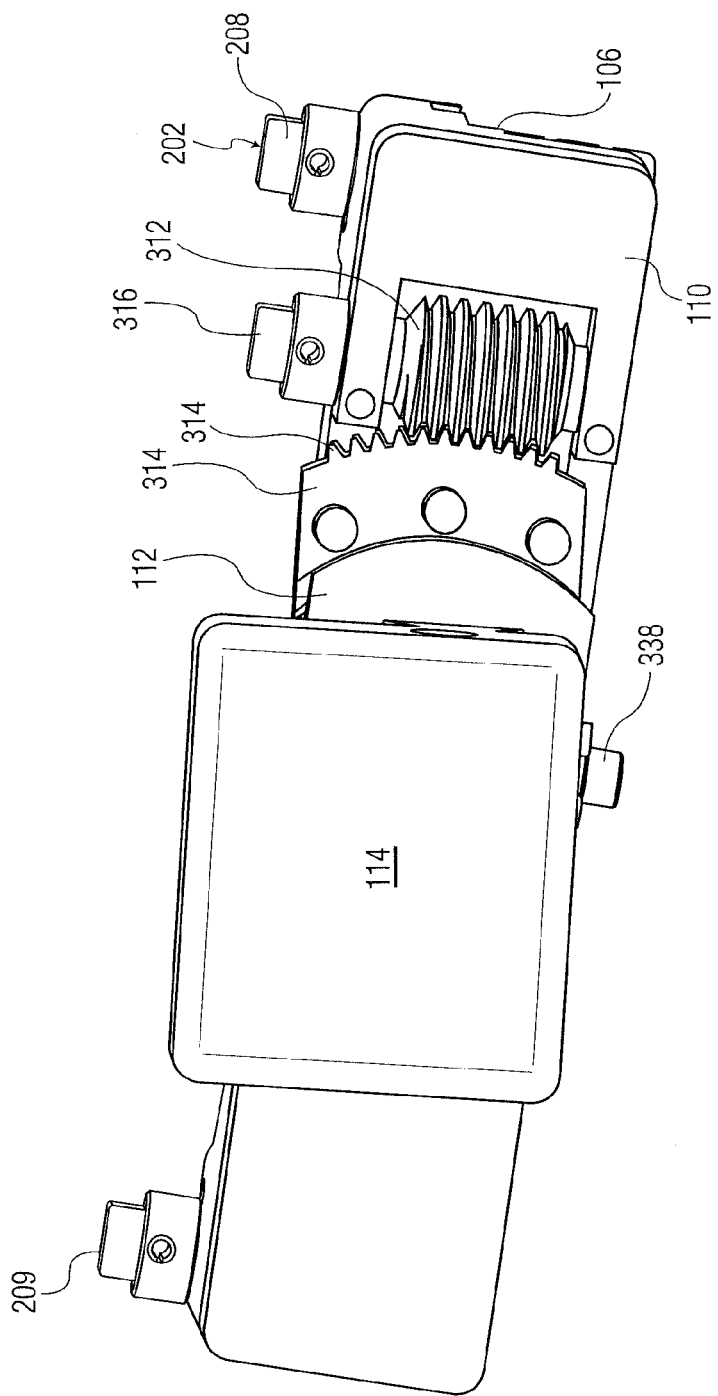
FIG. 3B is an isometric view from lines 3-3 of FIG. 2A and shows the internal gearing that enables a second member to pivot with respect to the ring element.

Referring to FIG. 3B in the preferred embodiment, second member 112 rotates through a range of angles by the interaction of a worm 312 (i.e., a gear in the form of a screw) with an arcuate worm gear 314 mounted on second member 112 on the outer surface of the portion thereof forming track 612 (i.e., a worm wheel). For example, worm 312 can thread into worm gear 314 causing second member 112 to rotate relative to first member 110. In use, a user rotates drive head 316 of worm 312 causing worm 312 to rotate while engaged with worm gear 314. Because first member 110 is attached to body 106 that is fixed to ring element 102, rotating worm 312 while engaged with worm gear 314 causes second member 112 to rotate upwardly or downwardly with respect to the plane of ring 102. Although described as a worm gear and worm any reasonable method can be used to change the angle of second member 112 with respect to first member 110. For example, the angle can be changed by spur gears, helical gears, double helical gears, bevel gears, crown gears, or any other gearing deemed suitable. Further increasing the number of threads (i.e., increasing the number of threads on the worm gear and worm) increases the number of rotations of user interface 316 required to move through a given angle. Thus, increasing the number of threads provides a greater level of precision during rotation.

Referring to FIGS. 2A and 6A, as shown, third member 114 is mounted on second member 112. While mounted on second member 112, third member 114 can move linearly with respect to second member 112. That is, third member 114 can linearly move along arms 108, 108' of the ring element in a direction parallel to the plane of ring 102 in an anterior-posterior direction.

Figure 3C:
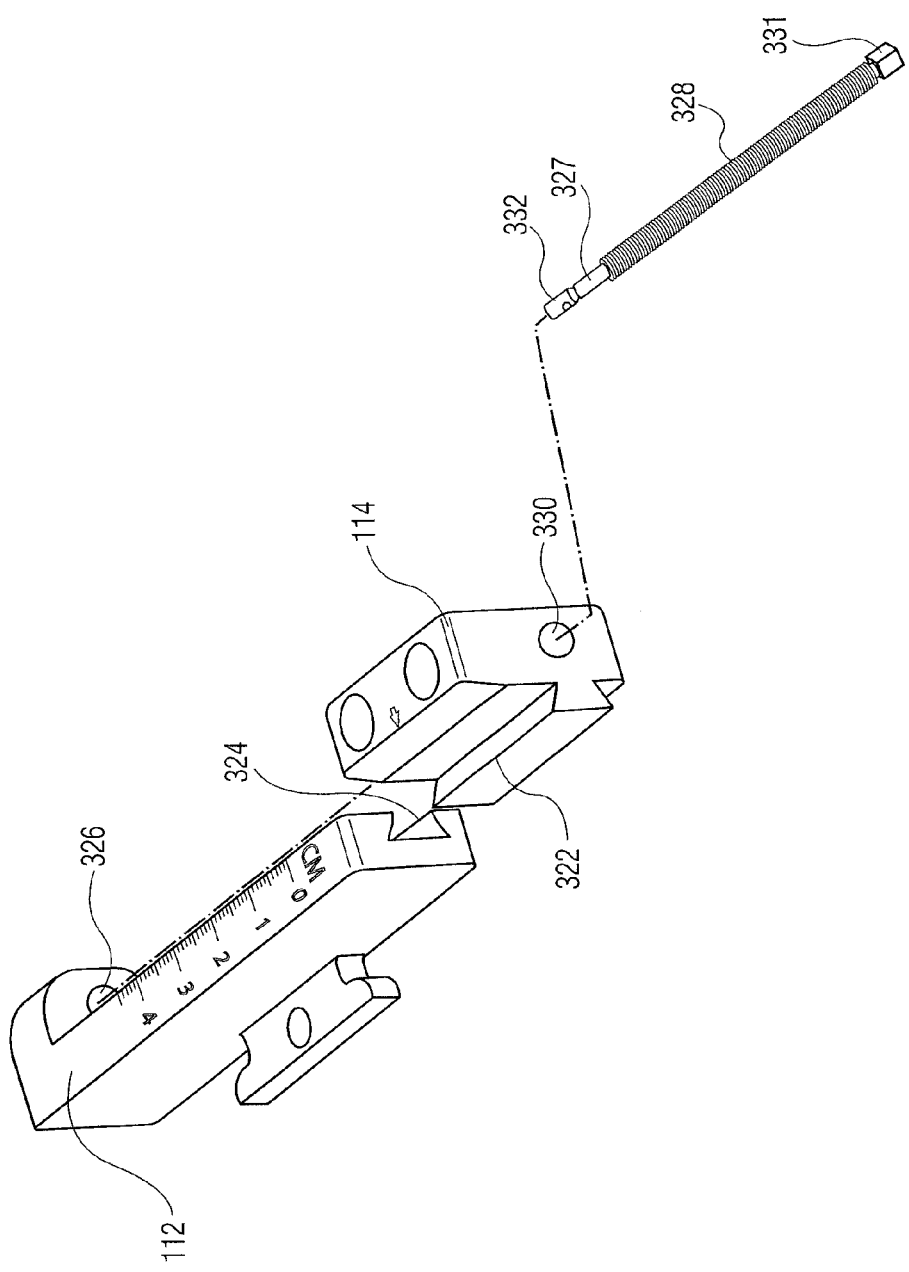
FIG. 3C is an exploded view of the moveable third member and second member shown in FIG. 2A as well as a threaded rod that enables the third member to move linearly with respect to the circumference of the ring element.

Referring to FIG. 3C in the preferred embodiments, third member 114 includes a dovetail protrusion 322 (i.e., guide element) that mates with a groove or dovetail 324 extending along second member 112. Protrusions 322 mates with groove or dovetail 324 thereby providing a guide for the linear motion. For example, in the preferred embodiment, a male dovetail protrusion 322 extending from third member 114 can mate with a female dovetail 324 located on second member 112 thereby providing a linear guide between second member 112 and third member 114. Any form of male and female guide elements can be used to provide a linear guide between third member 114 and second member 112.

Figure 3D:
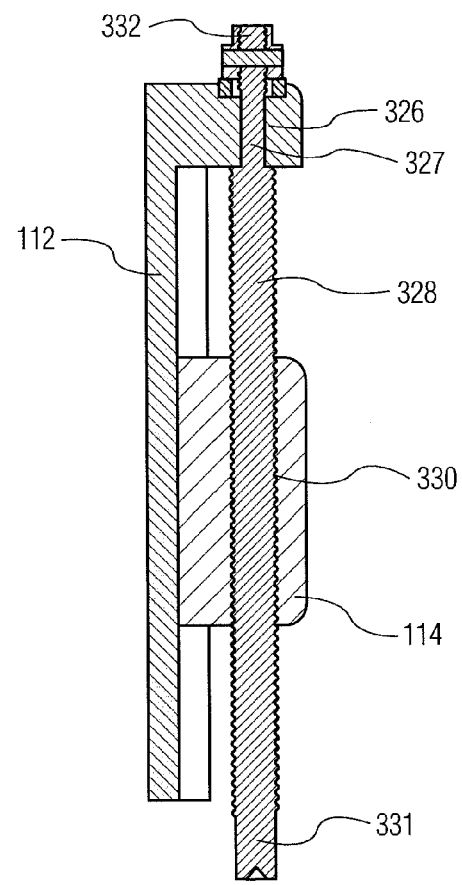
FIG. 3D is a cross-sectional view showing the member of FIG. 3C assembled.

Referring to FIGS. 3C and 3D, in the preferred embodiment, second member 112 includes a bore 326 for receiving an end 327 of a threaded rod 328. Further, third member 114 can translate on threaded rod 328 as it is rotated via drive head 331 or 332. Translation is possible because third member 114 includes a threaded bore 330 for receiving threaded rod 328. Thus, rotating threaded rod 328 translates third member 114 along the axis of threaded rod 328. In use, a user rotates drive head 331 or 332 causing threaded rod 328 to rotate in bore 330 of third member 114 thereby causing third member 114 to move linearly along arm 108, 108' of ring element 102. Alternately, any reasonable method for moving third member 114 linearly can be used. Further, increasing the number of threads/grooves on third member 114 and the number of threads/grooves on rod 328 increases the amount of precision in linearly moving third member 114. In the preferred embodiment, one rotation moves member 114 about one millimeter.

Referring to FIG. 4, the adjustable device having the first, second, and third member in a first position is illustratively depicted. As shown, first member 110 has not moved perpendicular to planar surface 206 of body 106. Further, second member 112 has not been rotated with respect to first member 110. Lastly, third member 114 is depicted in a first position.

Figure 5:
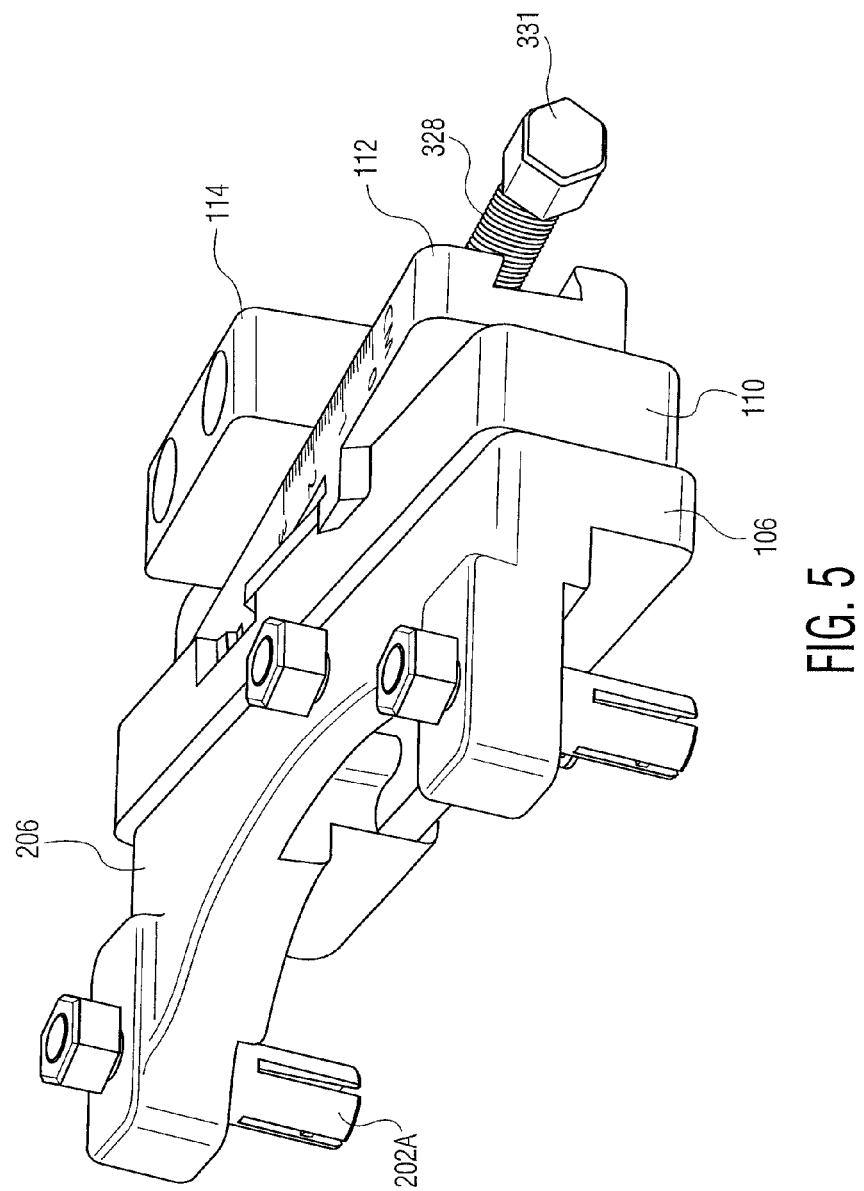
FIG. 5 is an isometric end view of the adjustable device of FIG. 4 in a second position.

Referring to FIG. 5, the relative displacement of each of the first, second, and third members is illustratively depicted as compared to FIG. 4. As shown, first member 110 has been displaced perpendicularly to planar surface 206 of body 106. Further, second member 112, has rotated with respect to first member 110. Lastly, third member 114 is depicted in a second position where it has moved linearly with respect to second member 112.

Figure 6B:
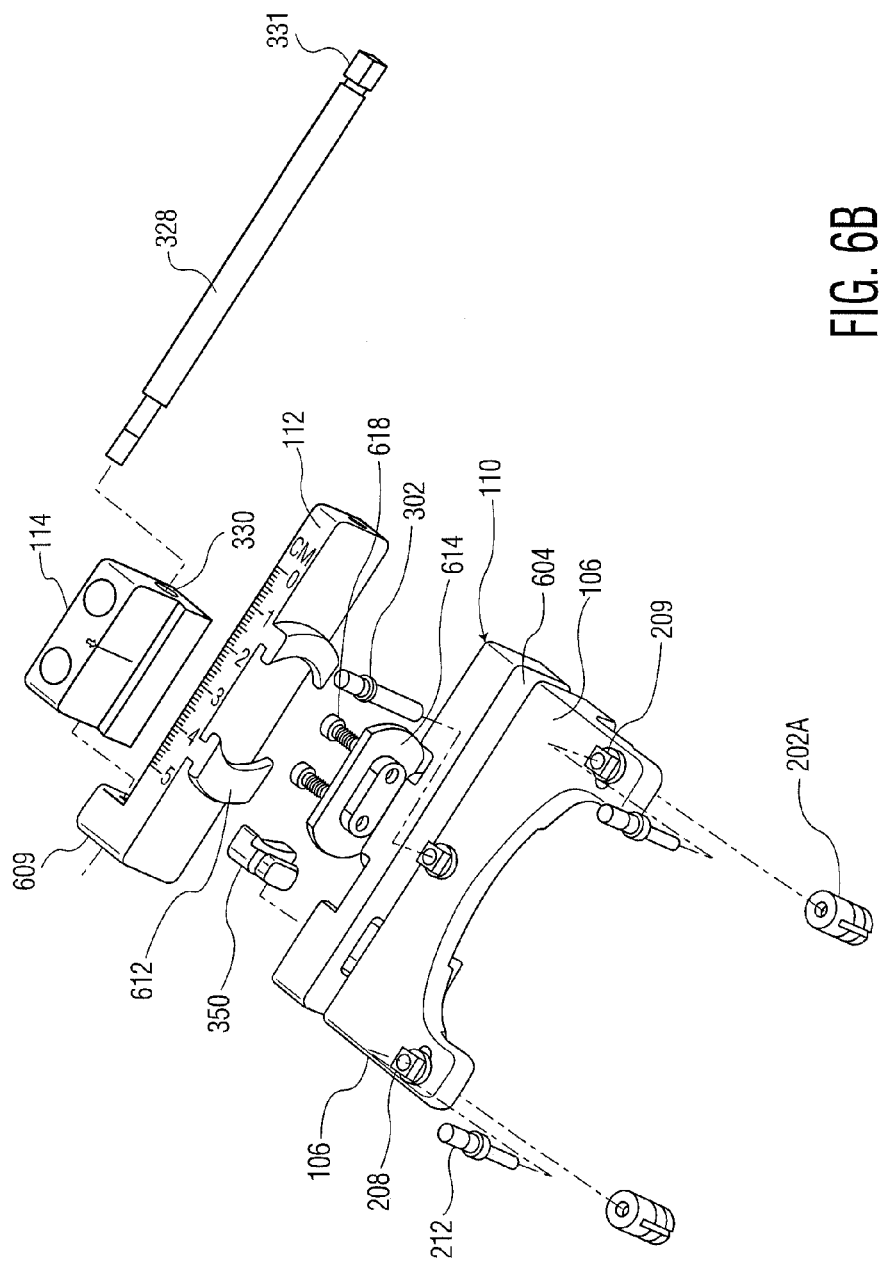

Referring to FIGS. 6A and 6B, there is shown an exploded view of adjustable device 104 of the preferred embodiment illustratively depicts the internal contact surfaces for each of body 106, first member 110, and second member 112. As shown, body 106 includes internal planar surface 602 which contacts internal planar surface 604 of first member 110. These planar surfaces provide a guide surface as first member 110 is displaced in a direction perpendicular to the plane of ring 102. Preferably, internal planar surfaces 602, 604 are substantially smooth surfaces permitting low friction sliding movement. Alternatively, in other instances, internal planar surfaces 602, 604 can include male and female protrusions (not shown) for allowing movement only perpendicular to planar surface 206 of body 106.

Further, as shown, internal planar surface 606 of first member 110 contacts an internal planar surface 608 of second member 112. Thus, during rotation these guide surfaces minimize motion in an undesired direction. Further, the angular motion of second member 112 is guided by track 612 which is in the form of an arcuate guide surface that rides on an arcuate guide element 614 which is attached to a planar surface 616 located on first member 110. Further, track 612 provides a center of rotation centrally located on first member 110. Disc 614 attaches to planar surface 616 by, for example, screws 618 threaded into holes 620 located in first member 110. Because track 612 rides on disc 614 motion in any direction other than the desired angular rotation direction is minimized. Gear teeth 315 are provided on the outer surfaces of track 612 which are driven by worm 312. A lock element 350 may be provided to lock second member 112 in the desired angular position.

Further, third member 114 includes a male dovetail protrusion 610 that mates with a female guide surface 609 acting as a guiding surface when third member 114 moves linearly. Each of the above described surfaces increase the control of the adjustable device by minimizing motion other than in the desired directions.

Figure 7B:
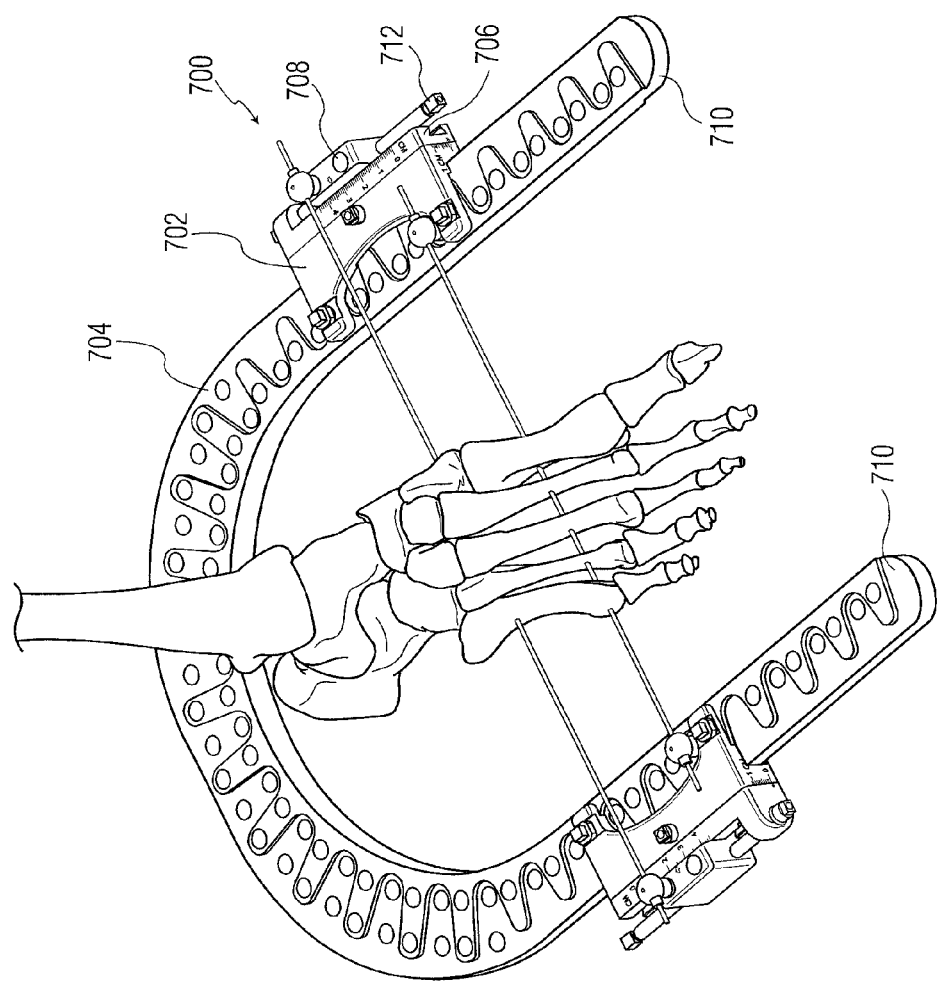

Referring to FIGS. 7A-7B, in some embodiments, adjustable device 104 can move only in the anterior-posterior and inferior-posterior directions. As shown, an alternate adjustable device 700 can include a body 702 attached to a ring element 704. Further mounted on body 702 is a first member 706 providing movement perpendicular to body 702 by rotation of screw 714 and a second member 708 mounted on first member 706 providing linear movement along arms 710 of ring element 704 by rotation of screw 712. In this embodiment there is no rotational movement between member 706 and 702.

As shown, unlike the preferred adjustable device capable of motion in three directions, the adjustable device of FIGS. 7A and 7B is only capable of movement in two directions. As depicted, first member 706 mounted on body 702 provides movement perpendicular to body 702. Further, second member 708 mounted on first member 706 provides motion parallel to the plane of the ring.

Further, in some embodiments, a scale can be located on at least one of first member 110 and second member 112. This scale can be used to determine the length of angular or linear displacement by the member. Further, a scale can be located on any of the body, first member, second member, or third member for respectively determining the amount of linear, angular, or circumferential movement of each of the members.

Figure 8B:
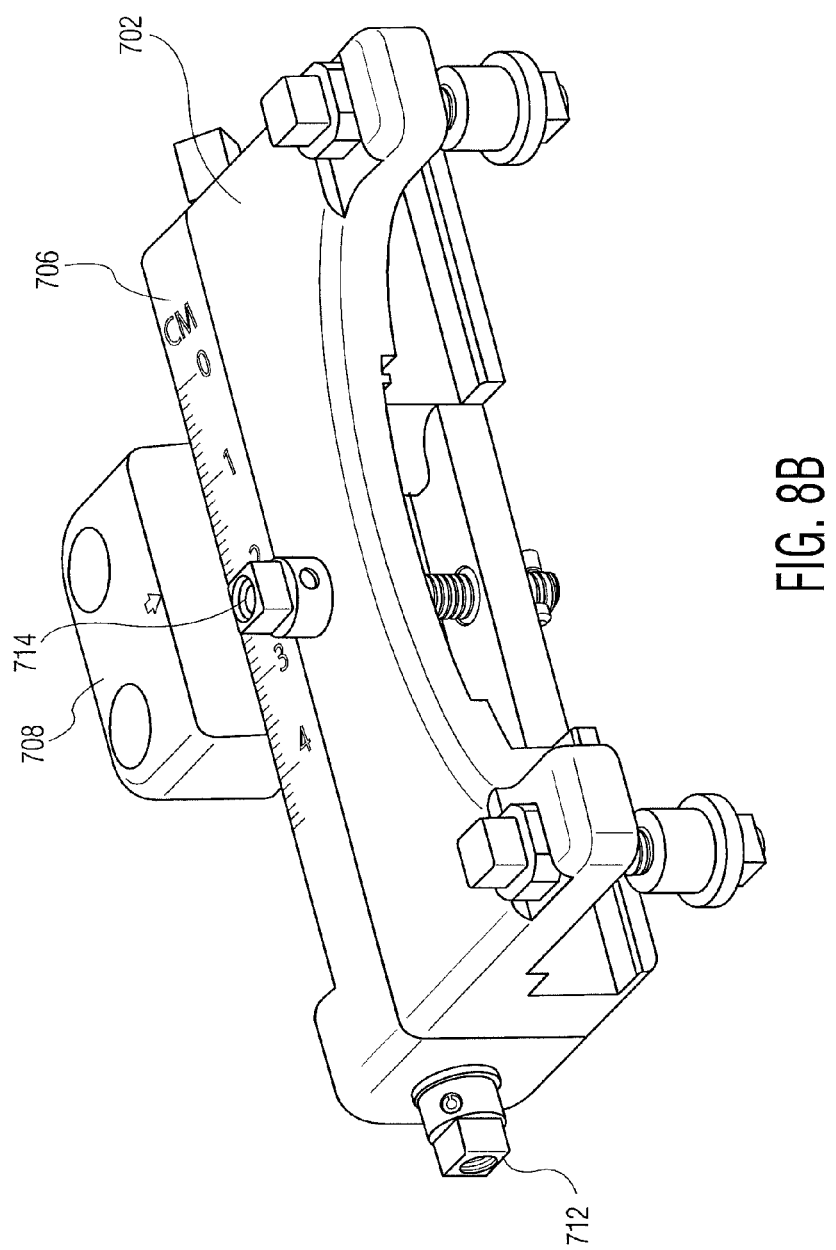
FIG. 8B is a side isometric view of the alternate adjustable device of FIG. 8A.
Figure 9:
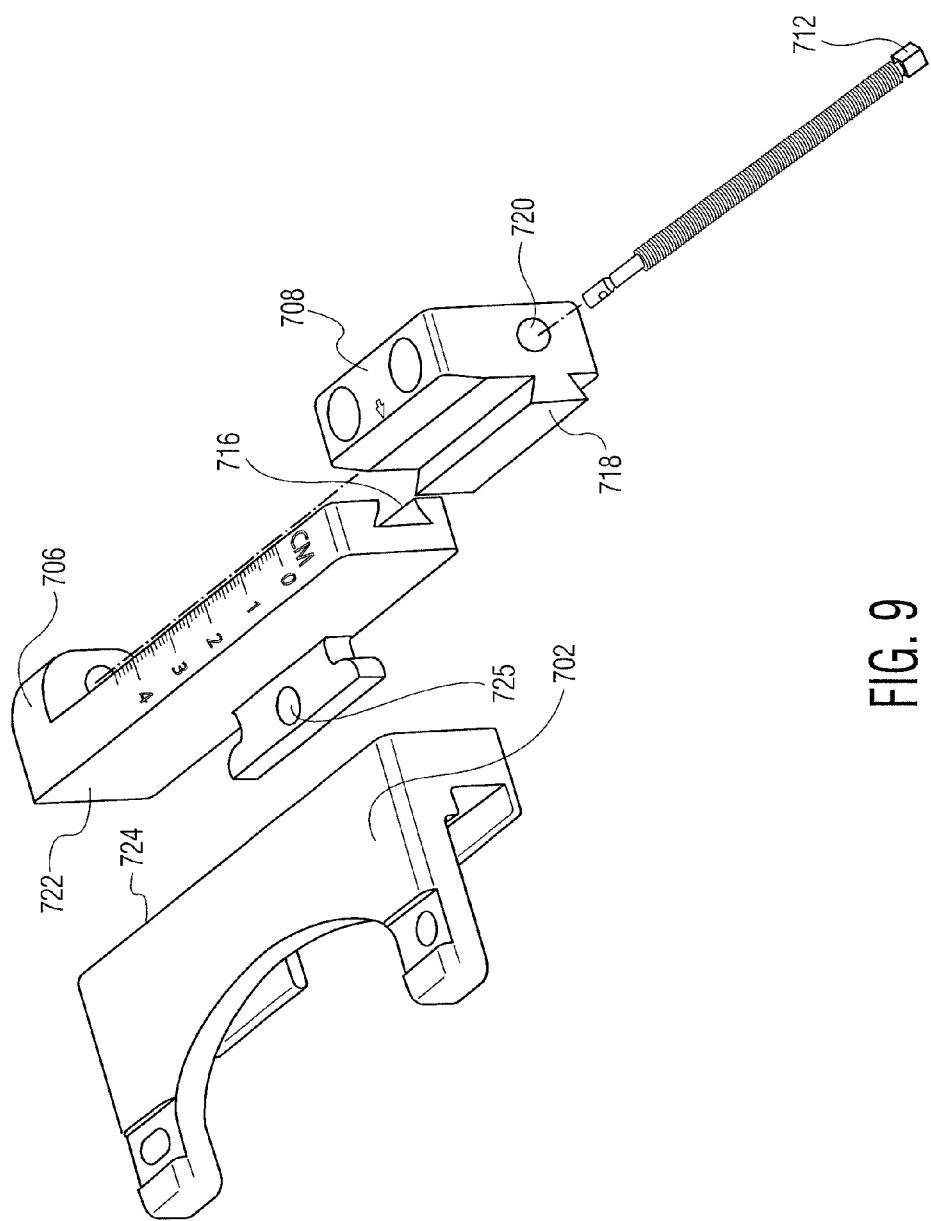
FIG. 9 is an exploded view of the alternate adjustable devices of 8A and 8B.

Referring to FIGS. 8A-9, there is shown an alternate adjustable device as shown in FIGS. 8A and 8B. The device generally denoted as 700 includes a body 702, first member 706 and second member 708 but does not provide rotational movement between member 706 and 702 as in adjustable device 104 (FIG. 5). Movement parallel to the ring is accomplished by turning screw shaft 712 to move element 708 and movement perpendicular to the ring is accomplished by turning screw shaft 714 and moving element 706 in relation to body 702. Pin holder can be located in one or both of holes 718.

FIG. 9 shows an exploded view of the alternate adjustable device 700 including body 702 and element 708 slidably mounted in a groove 716 in member 706 via a dovetail extension 728 and sliding element 708. Again, screw 712 is rotated in a threaded bore 720 of element 708 to cause the movement of element 708 parallel to the ring arm 710. Element 706 and body 702 includes contacting surfaces 722 and 724 respectively. These surfaces contact when the element 706 is moved in a direction perpendicular to the plane of the ring by turning screw 714 in threaded bore 725. This movement may be guide by tongue and groove interconnection as in device 104.

Figure 10:
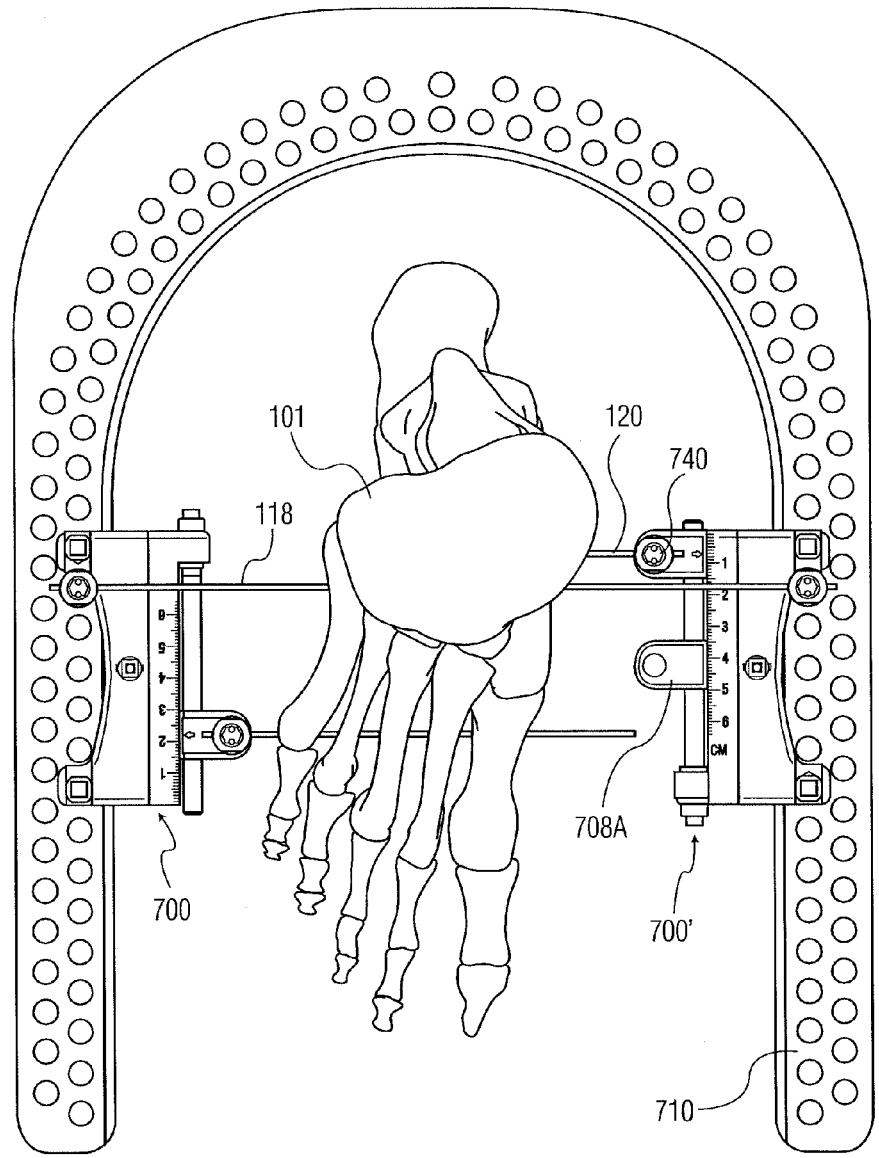
FIG. 10 is a top view of an alternate dynamic external fixator with adjustable members mounted on the inside of the rings.
Figure 11:
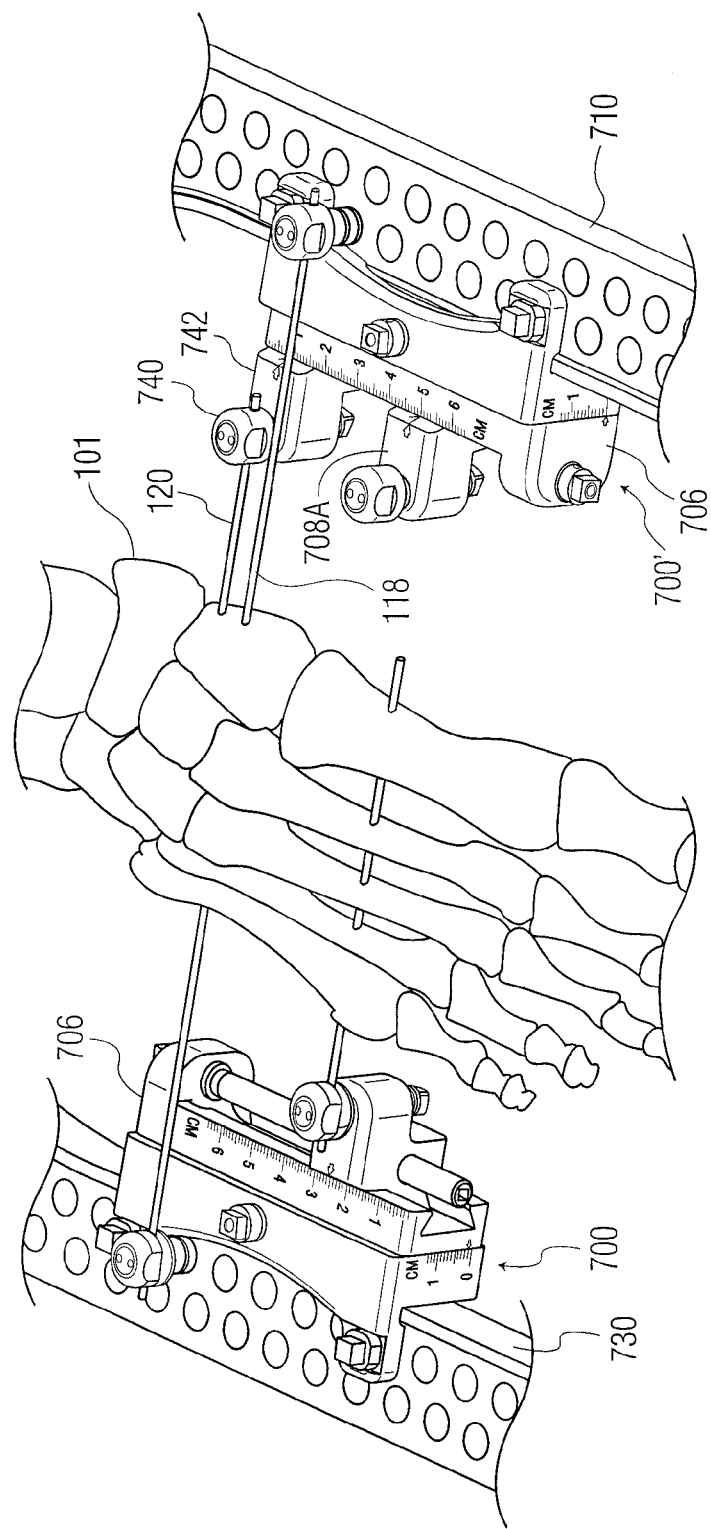
FIG. 11 is an enlarged isometric view of the ring and adjustable members of FIG. 10.

Referring to FIGS. 10 and 11, there is shown a top view of an alternate system in which the adjustable device 700 is mounted on the inner surface 730 of ring 704. Again, Kirschner wires 118 and 120 may be engaged with a foot 101.

Figure 12:
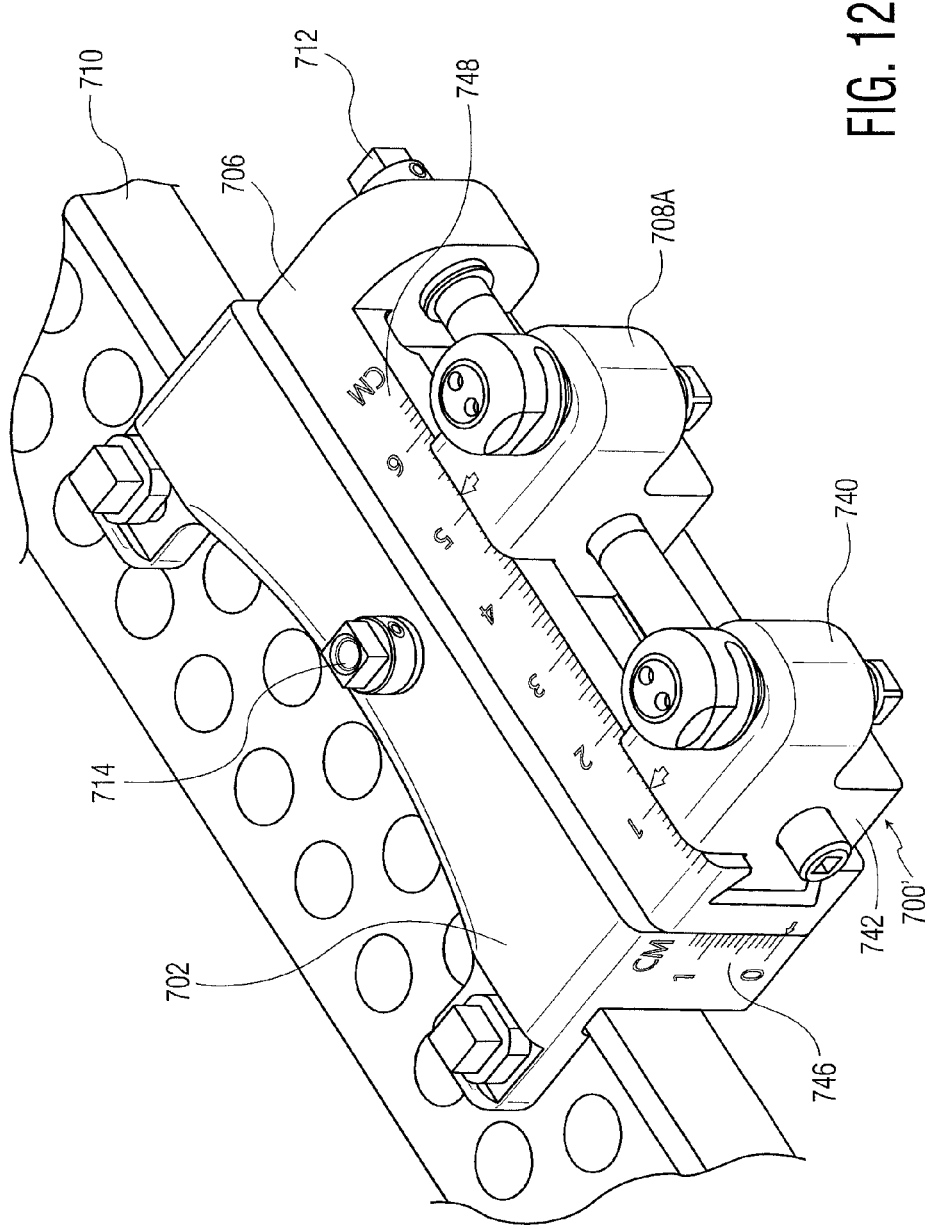
FIG. 12 is a top isometric view of an alternate adjustable device exhibiting two degrees of freedom.
Figure 13:
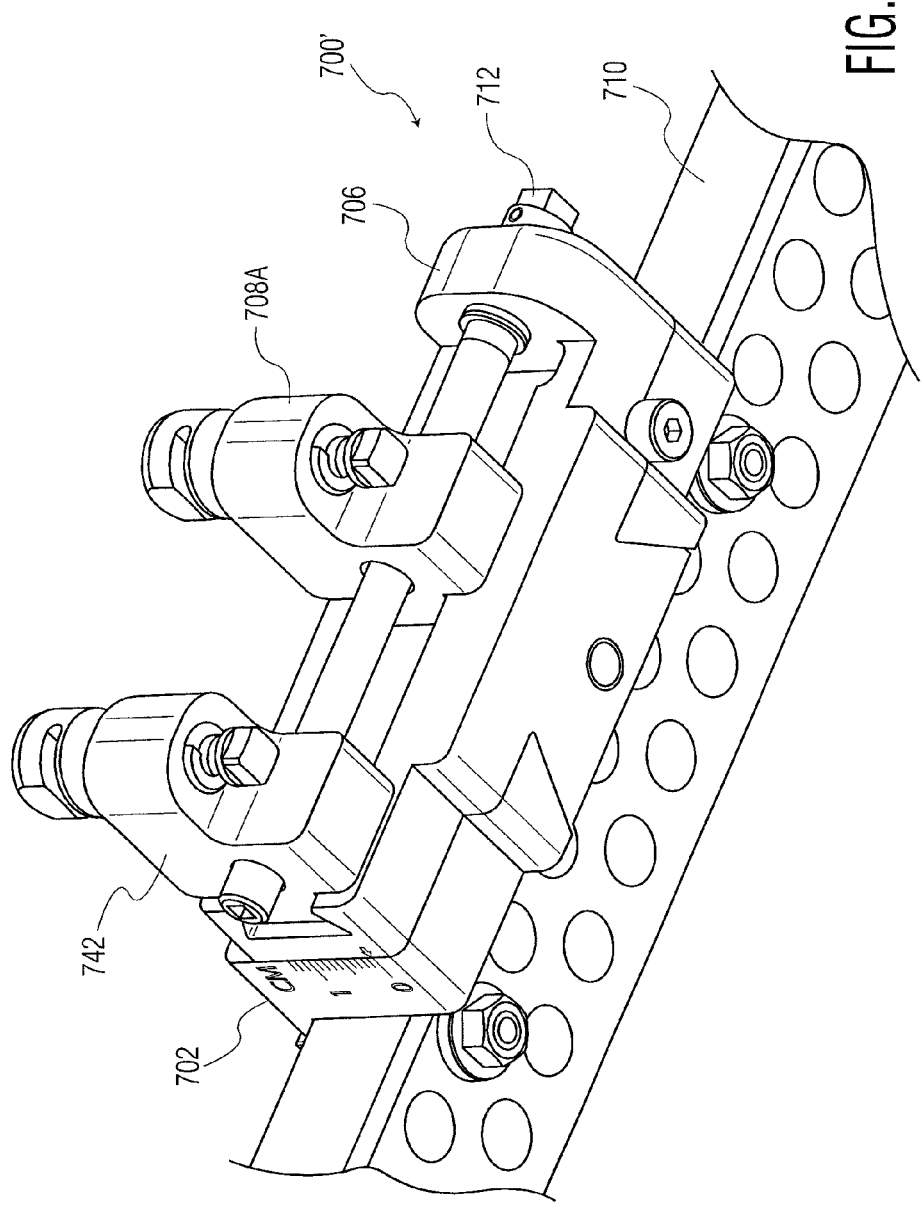
FIG. 13 is a bottom isometric view of the adjustable member of FIG. 12.

Referring to FIGS. 10 through 13, there is shown as an alternate adjustable device 700' which is similar to adjustable device 700 with the exception that a second pin holder 740 in addition to a first pin holder block 708A is attached to a block 742 which is slidably mounted within the groove 716 of element 706. Block 742 has a threaded bore which is mounted on screw shaft 712 and is moveable with respect to element 706. First block 708A is also provided with a pin holder and is operated as block 708. This allows the mounting of two Kirschner wires on element 706 with both Kirschner wires being adjustable along the length of the arm 710. Again, screw shaft 714 allows the block 706 to move in the direction perpendicular to the plane of arm 710. As shown in FIG. 12, indicators scales 746 and 748 may be provided to indicate the amount of movement of the Kirschner wires in millimeters.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. An external fixation system comprising:
a generally planar ring element extending along a first axis lying in a plane of the generally planar ring element;
an adjustable device having a body releasably mounted on the ring element, the body having first and second ends spaced along the first axis of the generally planar ring element, the adjustable device comprising:
a first member mounted on the body for movement thereon in a direction generally perpendicular to the plane of the ring element;
a second member pivotally mounted on the first member for angular movement relative thereto about a pivot axis extending in a direction nonparallel to the first axis of the ring element, a first drive screw mounted on the first member capable of engaging a drive element on the second member for pivoting the second member relative to the first member about the pivot axis;
a third member mounted on the second member for movement along a second axis extending between first and second ends of the second member, a second drive screw mounted on the second member and engaging a threaded bore in the third member, the threaded bore extends parallel to the second axis for moving the third member relative to the second member; and
a bone engaging element mounted on the third member, the third member located so that the bone engaging element can move intermediate the first and second ends of the body.

2. The external fixator as set forth in claim 1 wherein the first member includes arcuate guide surfaces for engaging an arcuate guide element on the second member for guiding the pivoted movement therebetween.

3. The external fixator as set forth in claim 2 wherein the arcuate guide surfaces have a center of rotation located on the first member.

4. The external fixator as set forth in claim 3 wherein the arcuate guide surfaces and guide element are in the form of a tongue and groove.

5. The external fixator as set forth in claim 2 further comprising a third drive screw extending between the first member and the body for moving the first member with respect to the body.

6. The external fixator as set forth in claim 1 wherein a linear guide surface is provided on the second member for engaging a guide element on the third member.

7. The external fixator as set forth in claim 6 wherein the guide surface and guide element are dovetail shaped.

8. The external fixator as set forth in claim 1, wherein the first member includes a first surface in contact with a second surface included on the second member and wherein these surfaces minimize movement other than angular movement.

9. The external fixator as set forth in claim 1, wherein the first member and the body include surfaces in contact with each other that minimize movement other than movement in a direction perpendicular to the planar ring element.

10. An external fixation system comprising:
a ring element having a surface extending along a first axis and defining a plane;
an adjustable device mounted on the ring element including a body, the body having first and second ends, a first member, a second member and a third member,
the body being releasably mounted on the ring element;
the first member being mounted on the body and capable of moving in a direction generally perpendicular to the plane of the ring element by relative rotation of a drive element and a first drive screw mounted on the body;
the second member mounted on the first member and capable of pivotal motion with respect to the first member and the ring element about a pivot axis extending along a direction non-parallel to the first axis lying in the plane of the ring element surface by rotation of a second drive screw mounted on the first member in a bore in the first member; and
the third member mounted on the second member, the second member having a third drive screw extending along a second axis, rotation of the third drive screw linearly moving the third member with respect to the second member between first and second ends of the second member by rotating the third drive screw mounted on the second member and engaging the third drive screw with a threaded bore in the third member, the threaded bore extends parallel to the second axis, a k-wire or half-pin mounted on the third member able to move intermediate the first and second ends of the body.

11. The external fixation device of claim 10, wherein the third member's linear motion with respect to the second member is guided by mating a male and female protrusion.

12. A method for realigning, compressing or distracting broken bones, comprising:
providing an external fixation device having a circumferentially extending planar ring member defining a first axis lying in a plane of the planar ring member;
fixing an adjustable device having a body with first and second ends to the ring member, the adjustable device having a first moveable member movably attached to the body, and a second moveable member movably attached to the first moveable member and a third moveable member moveably attached to the second moveable member, a first drive screw mounted on the body and engaging a drive element for moving the first moveable member, a second drive screw mounted on the first moveable member and engaging a second drive element on the second moveable member and a third drive screw mounted on the second moveable member for engaging a third drive element on the third moveable member;
inserting a k-wire or half pin through a first piece of a bone and affixing the k-wire or half pin to the ring member;
inserting a second k-wire through a second piece of bone and affixing the second k-wire to the third moveable member of the adjustable device; and
adjusting at least one of the first, second and third moveable members of the adjustable device with respect to the body by selectively rotating the first, second and third drive screws to realign, compress or distract the broken bones, the adjusting comprises moving the first moveable member in a direction generally perpendicular to the plane of the planar ring member by rotation of the first drive screw and pivoting the second moveable member with respect to the first moveable member about a pivot axis extending along a direction non-parallel to the first axis lying in the plane of the planar ring member by rotation of the second drive screw and moving the third moveable member mounted on the second moveable member along a second axis which extends between first and second ends of the second moveable member by rotating the third drive screw, the third drive screw mounted on the second moveable member and engaging a threaded bore in the third moveable member, the threaded bore extends parallel to the second axis, the second k-wire affixed to the third moveable member able to move intermediate the first and second ends of the body.

13. The method of claim 12, wherein the first moveable member is adjusted with respect to the body by moving the first moveable member in a direction perpendicular to the plane of the ring member by rotating the first drive screw.

14. The method of claim 13, wherein the second and third moveable members are adjusted by linearly moving the third moveable member with respect to the second moveable member by rotating the third drive screw.

15. The method as set forth in claim 13, wherein the second drive screw mounted on the first moveable member is capable of pivoting the second moveable member with respect to the first moveable member about the pivot axis.

\* \* \* \* \*